United States Patent
Zhou et al.

(10) Patent No.: US 10,550,138 B2
(45) Date of Patent: Feb. 4, 2020

(54) CHIRAL SPIRO PHOSPHORUS-NIROGEN-SULPHUR TRIDENTATE LIGAND, PREPARATION METHOD AND APPLICATION THEREOF

(71) Applicant: Zhejiang Jiuzhou Pharmaceutical Co., Ltd., Zhejiang (CN)

(72) Inventors: Qilin Zhou, Tianjin (CN); Jianhua Xie, Tianjin (CN); Denghui Bao, Tianjin (CN); Lixin Wang, Tianjin (CN)

( * ) Notice: Subject to any disclaimer, the term of this patent is extended or adjusted under 35 U.S.C. 154(b) by 285 days.

(21) Appl. No.: 15/572,160

(22) PCT Filed: Jan. 16, 2016

(86) PCT No.: PCT/CN2016/072087
§ 371 (c)(1),
(2) Date: Nov. 6, 2017

(87) PCT Pub. No.: WO2016/184160
PCT Pub. Date: Nov. 24, 2016

(65) Prior Publication Data
US 2018/0141966 A1    May 24, 2018

(30) Foreign Application Priority Data

May 15, 2015  (CN) .......................... 2015 1 0246052

(51) Int. Cl.
| | | |
|---|---|---|
| *B01J 37/04* | (2006.01) |
| *C07B 53/00* | (2006.01) |
| *C07C 29/145* | (2006.01) |
| *C07C 29/149* | (2006.01) |
| *C07C 67/31* | (2006.01) |
| *C07C 69/675* | (2006.01) |

(Continued)

(52) U.S. Cl.
CPC ........... *C07F 9/5022* (2013.01); *B01J 31/189* (2013.01); *B01J 31/226* (2013.01); *B01J 37/04* (2013.01);

(Continued)

(58) Field of Classification Search
CPC .................. C07F 9/5022; C07F 9/5054; C07F 9/655363; C07F 15/0033; B01J 31/189; B01J 31/226; B01J 31/249; B01J 37/04; B01J 2231/643; B01J 2531/0241; B01J 2531/827; C07B 53/00; C07C 29/145;

(Continued)

(56) References Cited

U.S. PATENT DOCUMENTS 8,962,839 B2    2/2015    Zhou et al.

FOREIGN PATENT DOCUMENTS

| CN | 101671365 A | 3/2010 |
|---|---|---|
| CN | 104892672 A | 9/2015 |

OTHER PUBLICATIONS

Xie et al., 6(3) Chemistry—An Asian J., 899-908 (2011) (CAS Abstract) (Year: 2011).*
English abstract; Chinese Application with Publication No. CN1112563A.
Chinese Application with Publication No. CN101671365A.
Angew Chem Int Ed vol. 54 Year 2015 p. 8791-8794.

* cited by examiner

*Primary Examiner* — Timothy R Rozof

(57) ABSTRACT

The present invention relates to a chiral spiro phosphine-nitrogen-sulfur (P—N—S) tridentate ligand, preparation method and application thereof. The P—N—S tridentate ligand is a compound represented by Formula I or Formula II, their racemates, optical isomers, or catalytically acceptable salts thereof. The ligand has a primary structure skeleton characterized as a chiral spiro indan skeleton structure with a thio group. The chiral spiro phosphine-nitrogen-sulfur tridentate ligand can be synthesized by reacting racemic or optical active compound 7-diaryl/alkyl phosphine-7'-amino-1, 1'-spiro-dihydro-indene compound having a spiro-dihydro-indene skeleton as the starting material. The chiral spiro P—N—S tridentate ligand being complex with transition metal salt can be used in an asymmetric catalytic hydrogenation reaction for catalyzing carbonyl compound. In particular, in asymmetric hydrogenation reaction process, being complex with iridium for catalyzing β-alkyl-β-keto ester can obtain a high catalytic activity (a catalyst amount of 0.0002% mol) and high enantioselectivity (up to 99.9% ee) result. So the present invention has a practical value for industrial and commercial production.

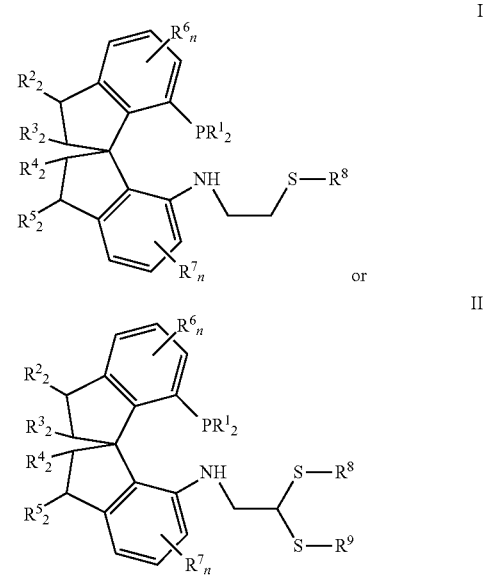

19 Claims, No Drawings

(51) Int. Cl.
   *C07C 69/708* (2006.01)
   *C07C 231/12* (2006.01)
   *C07C 231/18* (2006.01)
   *C07C 235/06* (2006.01)
   *C07C 269/06* (2006.01)
   *C07C 271/22* (2006.01)
   *C07F 9/50* (2006.01)
   *C07F 15/00* (2006.01)
   *B01J 31/18* (2006.01)
   *B01J 31/22* (2006.01)
   *C07F 9/6553* (2006.01)
   *B01J 31/24* (2006.01)

(52) U.S. Cl.
   CPC ............ *C07B 53/00* (2013.01); *C07C 29/145* (2013.01); *C07C 29/149* (2013.01); *C07C 67/31* (2013.01); *C07C 69/675* (2013.01); *C07C 69/708* (2013.01); *C07C 231/12* (2013.01); *C07C 231/18* (2013.01); *C07C 235/06* (2013.01); *C07C 269/06* (2013.01); *C07C 271/22* (2013.01); *C07F 9/5054* (2013.01); *C07F 9/655363* (2013.01); *C07F 15/0033* (2013.01); *B01J 31/249* (2013.01); *B01J 2231/643* (2013.01); *B01J 2531/0241* (2013.01); *B01J 2531/827* (2013.01)

(58) Field of Classification Search
   CPC ..... C07C 29/149; C07C 67/31; C07C 69/675; C07C 69/708; C07C 231/12; C07C 231/18; C07C 235/06; C07C 269/06; C07C 271/22
   See application file for complete search history.

CHIRAL SPIRO PHOSPHORUS-NIROGEN-SULPHUR TRIDENTATE LIGAND, PREPARATION METHOD AND APPLICATION THEREOF

This application is a national stage application based on PCT/CN2016/072087, filed on Jan. 26, 2016, which claims the priority of China Patent Application No. 201510246052.1, filed with the patent Office of China on May 15, 2015, titled "Chiral spiro phosphorus-nitrogen-sulphur tridentate ligand, and preparation method and application thereof", the contents of which are incorporated herein by reference in its entirety.

FIELD OF THE INVENTION

The present invention relates to a chiral spiro phosphine-nitrogen-sulfur (P—N—S) tridentate ligand, preparation method and application thereof. In particular to a preparation method for a kind of chiral spiro phosphine-nitrogen-sulfur compound which having spiro skeleton structure, and to the application in the asymmetric catalytic hydrogenation reaction of carbonyl compound. The present invention belongs to the organic synthesis technical field.

BACKGROUND OF THE INVENTION

The asymmetric reaction catalyzed by chiral transition metal complexes is the most effective method to obtain optically active chiral compounds, and has been widely used in the industrial production of chiral drugs. In asymmetric catalytic reaction, High-efficiency and high-selectivity results can be realized for synthesizing chiral compounds with the key chiral ligands or catalysts to be used. For this reason, in the past decades of researching, the development of new high-efficiency and high-selectivity chiral ligands and their catalysts has always been of concern.

As far as now, for ligands which were used very common and frequency in asymmetric catalytic hydrogenation reactions in industrial production, so far there have been thousands of chiral ligands and their catalysts reported in the literature, however, with little successful results come out. So the catalysts both with high catalytic activity (the TON value is up to 100,000) and high enantioselectivity (the ee value >99%) are still few and scarce (Zhou, Q.-L. Eds, Privileged Chiral Ligands and Catalysis, Wiley-VCH: 2011; Caprio, V.; Williams, J. M. J., Eds, Catalysis in Asymmetric Synthesis; Wiley-VCH: Chichester, 2009; de Vries, J. G.; Elsevier, C. J. Eds.; The Handbook of Homogeneous Hydrogenation; Wiley-VCH: Weinheim, 2007). Recently, our research group has designed and synthesized a kind of chiral spiro-pyridylamidophosphine tridentate ligand Spiro PAP with novelty structure (Xie, J.-H.; Liu, X.-Y.; Xie, J.-B.; Wang, L.-X.; Zhou, Q.-L. Angew. Chem. Int. Ed. 2011, 50, 7329-9332. Zhou Qilin, Xie Jianhua, Liu Xiaoyan, Xie Jianbo, Wang Lixin CN102040625A), its iridium complex Ir-Spiro PAP has a very prominent performance in the asymmetric catalytic hydrogenation reaction of carbonyl compounds, and the enantioselectivity value can be up to 99% ee, the TON value can be up to 4.50 million. The iridium catalyst Ir-Spiro PAP of the chiral spiro-pyridylamidophosphine tridentate ligand is also very effective for the asymmetric catalytic hydrogenation reaction of β-keto esters with the enantioselectivity value up to 99% ee and the TON value can be up to 1.23 million (Xie, J.-H.; Liu, X.-Y.; Yang, X.-H.; Xie, J.-B.; Wang, L.-X.; Zhou, Q.-L. Angew. Chem. Int. Ed. 2012, 51, 201-203). However, the chiral spiro iridium catalyst Ir-Spiro PAP only has a high enantioselectivity for β-aryl-β-keto ester, it just has a moderate enantioselectivity for β-alkyl-β-keto ester (<60% ee).

At present, the catalyst which has high-performance in asymmetric catalytic hydrogenation of β-alkyl-β-keto ester is limited to the ruthenium halide catalyst of chiral diphosphonic ligand, but the TON value of the most catalysts are not beyond ten thousand. And they were often required to add hydrochloric acid and other additives, which are corrode to metal reactors (Ohkuma, T.; Noyori, R. in Handbook of Homogeneous Hydrogenation, Eds.: de Vries, J. G.; Elsevier, C. J., Wiley-VCH, Weinheim, 2007, pp. 1105).

Therefore, Considering the importance application of asymmetric catalytic hydrogenation reaction of β-alkyl-β-keto ester in synthesizing chiral drugs, designing and developing novelty high-efficiency chiral ligands and catalysts can still be very significant although full of difficulty and challenge.

SUMMARY OF THE INVENTION

The objection of the present invention is to provide a chiral spiro phosphine-nitrogen-sulfur (P—N—S) tridentate ligand, and preparation method and application thereof. Such chiral spiro tridentate ligand are designed based on the relationship between the structure of the iridium catalyst Ir-Spiro PAP of chiral spiro-pyridylanidophosphine tridentate ligand with its enanio selectivity and catalytic activity in the asymmetric catalytic hydrogenation reaction of carbonyl compound. Introducing the thioether group into the chiral spiro-amidophosphine ligand SpiroAP (Xie, J.-B.; Xie, J.-H.; Liu, X.-Y.; Kong, W.-L.; Li, S.; Zhou Q.-L. J. Am. Chem. Soc. 2010, 132, 4538-4539. Zhou Qilin, Xie Jianhua, Xie Jianbo, Wang Lixin CN101671365A) makes it a novel phosphine-nitrogen-sulfur tridentate ligand, and significantly improves the chiral control from the catalyst to the substrate. In addition, it obtains excellent enantioselectivity (up to 99.9% ee) and up to 0.35 million turnover number (TON). The present invention provides a novel catalytic product compared to the existed chiral ligands and their catalysts when applying them in asymmetric hydrogenation of carbonyl compounds.

The chiral spiro phosphine-nitrogen-sulfur (P—N—S) tridentate ligand provided in the present invention is a compound having a structure of Formula I or Formula II, their racemates, optical isomers, or catalytically acceptable salts thereof.

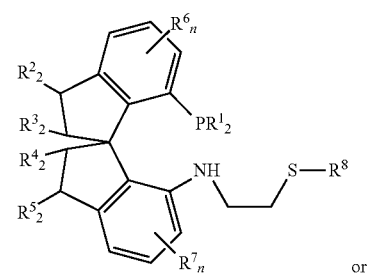

or

-continued

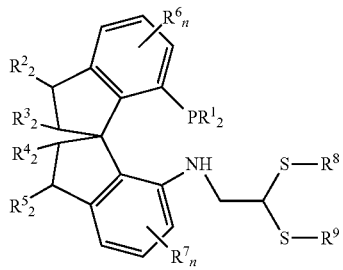

wherein, $R^1$ is selected from $C_1$-$C_{10}$ alkyl, phenyl, substituted phenyl, 1-naphthyl, 2-naphthyl, heteroaryl or benzyl, and the substituent on said phenyl is $C_1$-$C_{10}$ alkyl or alkoxyl, with a substituent amount ranging from 1~5, and said heteroaryl is furyl, thienyl or pyridyl;
$R^2$, $R^3$, $R^4$ and $R^5$ are independently selected from H, $C_1$-$C_{10}$ alkyl, phenyl, substituted phenyl, 1-naphthyl, 2-naphthyl, heteroaryl or benzyl, and the substituent on said phenyl is $C_1$-$C_{10}$ alkyl or alkoxyl, with a substituent amount ranging from 1~5, and said heteroaryl is furyl, thienyl or pyridyl; $C_1$-$C_{10}$ alkoxyl; or $R^2$~$R^3$, $R^4$~$R^5$ are incorporated into $C_3$-$C_7$ aliphatic ring, aromatic ring; $R^2$, $R^3$, $R^4$ and $R^5$ can be the same or different;
$R^6$, $R^7$ are independently selected from H, $C_1$-$C_{10}$ alkyl, $C_1$-$C_{10}$ alkoxy, $C_1$-$C_{10}$ alphatic amido group, and n=0~3; or when n≥2, two adjacent $R^6$ groups or two adjacent $R^7$ groups can be incorporated into a $C_3$-$C_7$ aliphatic ring or aromatic ring and $R^6$, $R^7$ can be same or different.
$R^8$, $R^9$ are independently selected from $C_1$-$C_{10}$ alkyl, $C_1$-$C_{10}$ alkoxy, phenyl, substituted phenyl, 1-naphthyl, 2-naphthyl, heteroaryl or benzyl, and the substituent on said phenyl is $C_1$-$C_{10}$ alkyl or alkoxyl, with a substituent amount ranging from 1~5, and said heteroaryl is furyl, thienyl or pyridyl; or $R^8$ and $R^9$ groups can be incorporated into a ring by $C_2$-$C_4$ carbon chain, carbon chain containing N, O, S, aromatic nucleus or heterocyclic aromatic ring; $R^8$, $R^9$ can be the same or different.

The present invention provides the synthesis methods for a chiral phosphine-nitrogen-sulfur tridentate ligand. the ligand is obtained by reacting racemic or optical active compound 7-diary/alkyl phosphine-7'-amino-1, 1'-spiro-dihydro-indene shown as Formula 1 having a chiral spiro-dihydro-indene skeleton as the starting material via the following reactions:

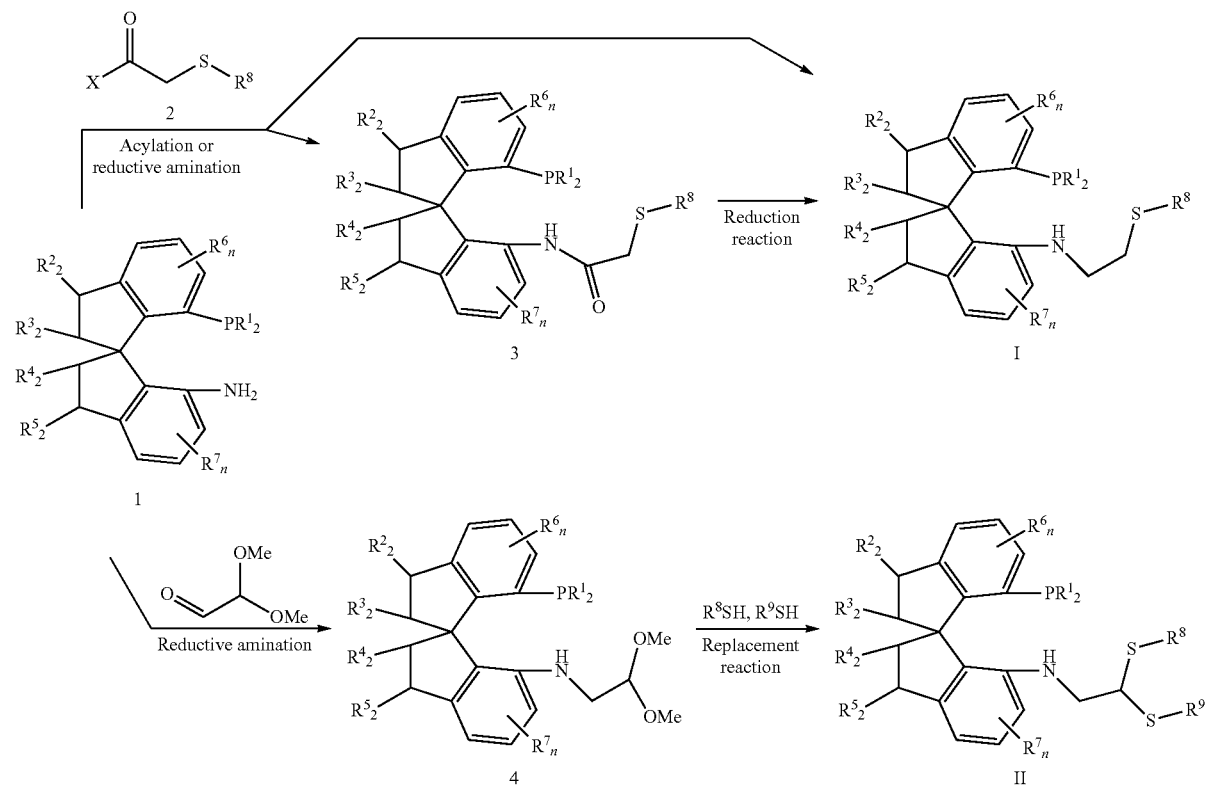

wherein, $R^1$~$R^9$ of Formula 1, 2, 3, 4 are defined as above, X of Formula 2 is H, Cl, Br, imidazole or hydroxide radical; the compound shown as Formula I having a chiral spiro-dihydro-indene skeleton is synthesized by the method according to the prior literature references (Jian-Bo Xie, Jian-Hua Xie, Xiao-Yan Liu, Wei-Ling Kong, Shen Li, Qi-Lin Zhou, J. Am. Chem. Soc. 2010, 132, 4538; Zhou Qilin, Xie Jianhua, Xie Jianbo, Wang Lixin, CN 101671365A).

The synthesis method for a chiral spiro phosphine-nitrogen-sulfur tridentate ligand is described as follows:

The compound of Formula 1 is firstly reacted with the compound of Formula 2 (X is neither H nor OH) in a reactor for 2~24 hours in the presence of organic solvents and alkalis to obtain the compound shown as Formula 3; the compound of Formula 3 is then reduced to obtain the chiral spiro phosphine-nitrogen-sulfur tridentate ligand having the structure of Formula I; or the compound of Formula 1 is reacted with the compound of Formula 2 (X is H) in a reactor for 2~24 hours in the presence of organic solvents and reducing agents directly to obtain the chiral spiro phosphine-nitrogen-sulfur tridentate ligand having the structure of Formula I; the molar ratio among said compound of Formula 1, Formula 2 and reducing agents is in a range of 1:1~5:1~10; the temperature of the reaction is −20~120° C.

Or the compound of Formula 1 is firstly reacted with the compound of Formula 2 (X is OH) in a reactor for 2~24 hours in the presence of organic solvents, alkalis and hydroxyl activators to obtain the compound shown as Formula 3; the compound of Formula 3 is then reduced to obtain the chiral spiro phosphine-nitrogen-sulfur tridentate ligand having the structure of Formula I; the molar ratio among said compound of Formula 1, Formula 2, hydroxyl activators and reducing agents is in a range of 1:1~5:1~10:1~10; the temperature of the reaction is −20~120° C.

Or the compound of Formula 1 is firstly reacted through reduction and amination with the glyoxal-dimethyl-carboxy aldehyde in a reactor in the presence of organic solvents and reducing agents to obtain the compound shown as Formula 4; the compound of Formula 4 is then reacted through replacement reaction with mercaptan ($R^8SH$ and $R^9SH$) in the presence of Lewis acids to obtain the chiral spiro phosphine-nitrogen-sulfur tridentate ligand having the structure of Formula II; the molar ratio among said compound of Formula 1, glyoxal-dimethyl-carboxy aldehyde, Lewis acids and mercaptan is in a range of 1:1~5:0.1~5:1~10; the temperature of the reaction is −10~120° C.

In the above synthesis method, the said organic solvent can be any one of methanol, ethanol, propanol, isopropanol, butanol, tetrahydrofuran, toluene, xylene, methyl tert-butyl ether, diethyl ether, dioxane, N,N-dimethyl-formamide, dimethyl sulfoxide, dichloromethane, chloroform, 1,2-dichloroethane or any mixture thereof said reducing agent can be lithium aluminium hydride, sodium borohydride, sodium triacetyl borohydride or sodium cyanoborohydride; said alkali is an organic base or an inorganic base, in which said organic base can be pyridine, triethylamine, tributyl amine, N-methylmorpholine or N,N-diethyl isopropyl amine; said inorganic base can be sodium hydroxide, potassium hydroxide, sodium carbonate or potassium carbonate; said carboxyl-activating reagent is ethyl chloroformate, isopropyl chloroformate, N, N'-dicyclohexyl-carbodimide or carbonyl diimidazole; said Lewis acid can be titanium tetrachloride, boron trifluoride, indium trichloride, zirconium tetrachloride, tellurium tetrachloride, silicotungstic acid, copper sulfate etc.

The chiral spiro phosphine-nitrogen-sulfur tridentate ligand according to the present invention is reacted in the asymmetric catalytic hydrogenation reaction to obtain carbonyl compounds, the said carbonyl compounds are selected from β-ketoester compound, β-ketoamide compound, or simple ketone compound.

As a preferred aspect, the said chiral spiro phosphine-nitrogen-sulfur tridentate ligand is reacted with the transition metal to obtain a complex, further reacted to obtain carbonyl compounds through the asymmetric catalytic hydrogenation reaction, the said carbonyl compounds are selected from β-ketoester compound, β-ketoamide compound, simple ketone compound.

As a preferred aspect, the said chiral spiro phosphine-nitrogen-sulfur tridentate ligand is reacted with an transitional metal salt under an inert gas atmosphere at a temperature of 25~120° C. for 0.5~4 hours in the presence of organic solvents; and then stirred for 0.1~3 hours under the hydrogen atmosphere at the pressure of 0.1~50 atm to obtain the complex of a chiral spiro phosphine-nitrogen-sulfur tridentate ligand and an transitional metal salt.

As a further preferred method, the molar ratio among the said chiral spiro phosphine-nitrogen-sulfur tridentate ligand and the transitional metallic salt is in a range of 1:1~2:1, and 1.5:1~2:1 is the most preferable.

As a more preferred method, the said transitional metal salt is a metal salt of iridium; the said iridium metal salt is [Ir(COD)Cl]$_2$ (COD=Cyclooctadiene), [Ir(COD$_2$)]BF$_4$, [Ir(COD)$_2$]PF$_6$, [Ir(COD)$_2$]SbF$_6$ or [Ir(COD)$_2$]OTf.

As a further preferred aspect, the above organic solvent is any one of methanol, ethanol, propanol, isopropanol, butanol, tetrahydrofuran, toluene, methyl tert-butyl ether, dioxane, DMF, DMSO or any mixture thereof.

As a further preferred aspect, to the obtained ligand solutions, was added carbonyl compounds and alkalis, the hydrogenation reaction was carried out under the hydrogen atmosphere at the pressure of 0.1~100 atm and at the temperature of 0~80° C. The molar ratio among the said carbonyl compounds and the said ligands is in a range of 100:1~500000:1. The concentration of the substrate is 0.001~10.0 M. The concentration of the said alkali is 0.005 M~1.0M. The said alkali is selected from sodium hydroxide, potassium hydroxide, sodium carbonate, potassium carbonate, sodium ethoxide, potassium ethoxide, sodium tert-butoxide, potassium tert-butoxide, lithium tert-butoxide, triethyl amine, tributyl amine or N-methyl morpholine.

As a further preferred aspect, the said chiral spiro phosphine-nitrogen-sulfur tridentate ligand is selected from the structures as follows, their racemates, optical isomers or catalytically acceptable salts thereof:

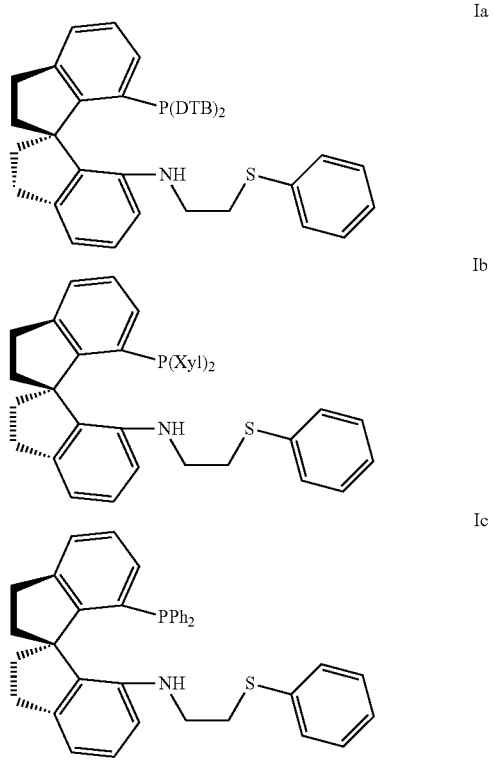

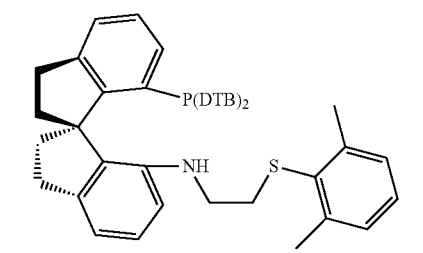
Id
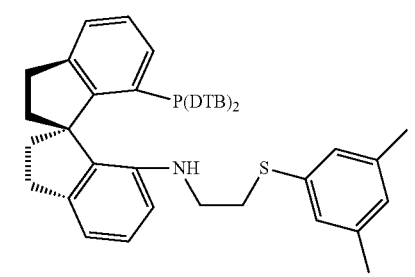
Ie
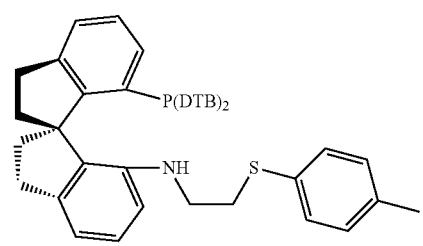
If
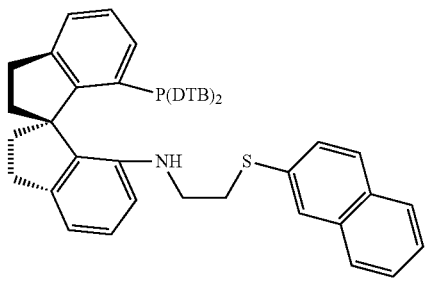
Ig
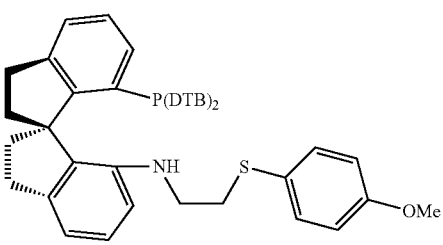
Ih
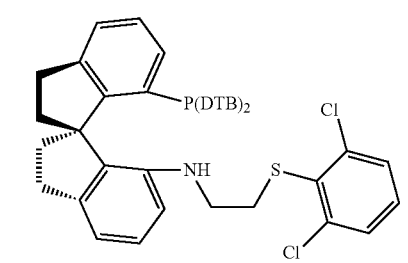
Ii
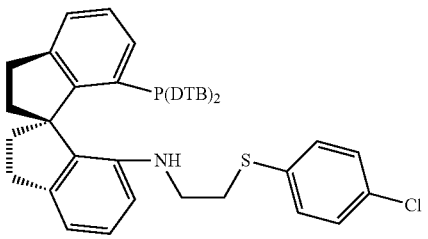
Ij
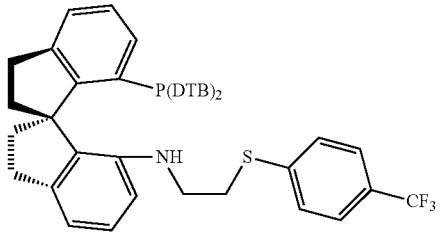
Ik
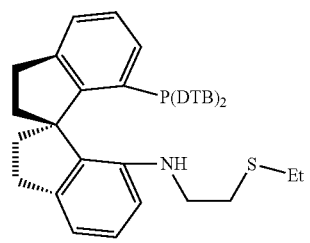
Il
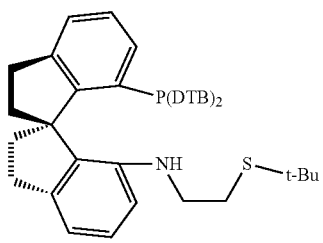
Im
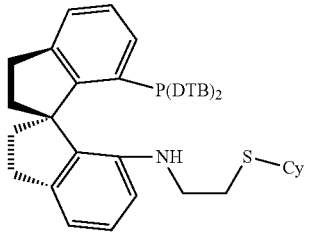
In
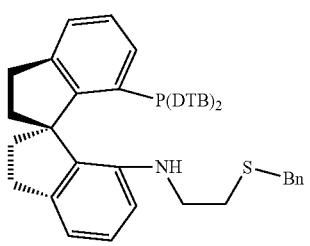
Io -continued

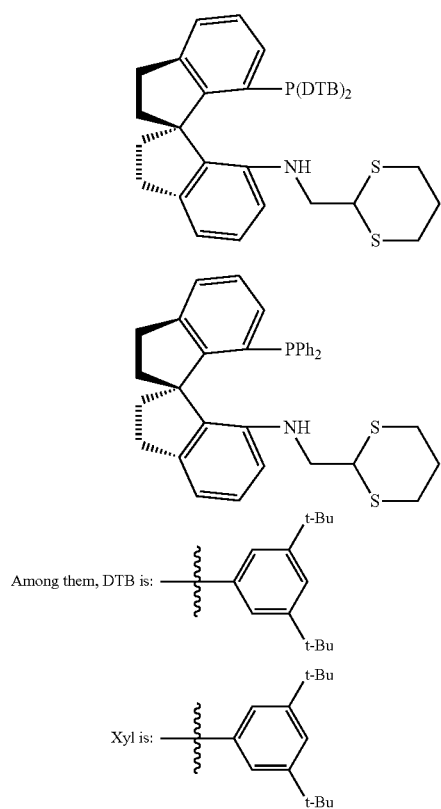

The spiro phosphine-nitrogen-sulfur tridentate ligand provided in the present invention has the main structure skeleton characterized as chiral spiro-dihydro-indene skeleton with a thioether group. It can be used as the chiral ligand in the iridium-catalyzed asymmetric catalytic hydrogenation reaction of carbonyl compounds such as aryl alkyl ketones, ketones, β-keto esters and β-keto-amides with an extremely high yield (>90%) and enantioselectivity (up to 99.9% ee). What's more, result such as high reaction activities and up to 0.35 million turnover numbers has been achieved. Compared to prior arts, the present invention has the following significant advantages:

1) The spiro phosphine-nitrogen-sulfur tridentate ligand herein when complex with transition metal salts has high catalytic reaction activity and high enantioselectivity in the asymmetric hydrogenation reaction of carbonyl compounds such as ketoesters. Particularly, so far, result such as the highest TON value has been achieved in the asymmetric hydrogenation reaction of β-alkyl-β-keto ester compound.

2) The preparation method for synthesizing the chiral phosphine-nitrogen-sulfur tridentate ligand herein is simple. It can be further used as a chiral ligand for the asymmetric hydrogenation reaction of carbonyl compounds with a mild reaction condition, high-efficiency, suitable for industrialization and commercial values.

DETAILED EMBODIMENTS

In order to further understand the present invention, preferable embodiments of the present invention will be described by reference to the examples, but it should be appreciated that these descriptions are merely intend to further illustrate the features and advantages of the present invention, rather than limiting the claims of the invention.

Example 1

Synthesis of (R)-7'-(bis(3,5-di-tert-butylphenyl) phosphino)-N-(2-(phenylthio)ethyl)-2,2',3,3'-tetra-hydro-1,1'-spirobi[inden]-7-amine (Ia)

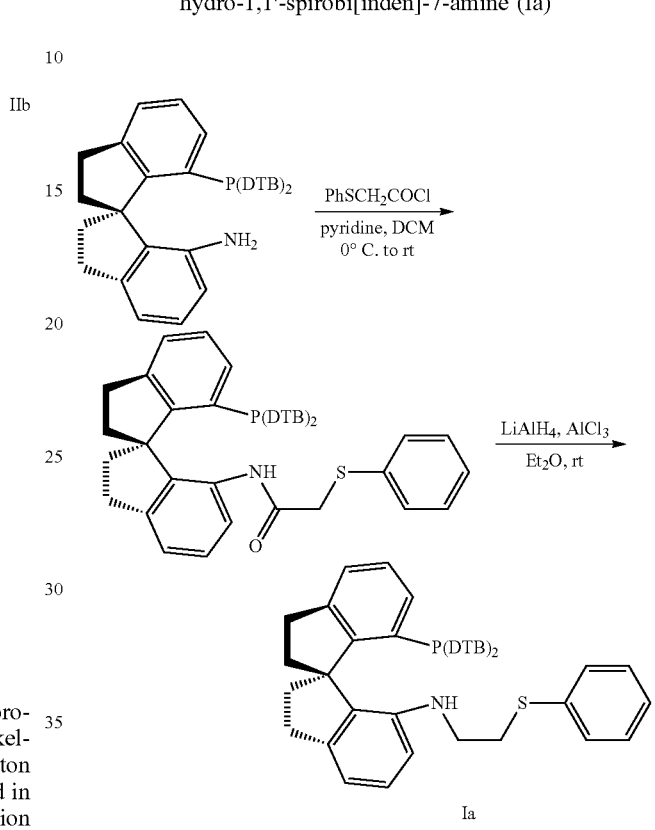

(R)-7-bis-(3,5-di-tert-butylphenyl) phosphino-7-amino-1, 1-spiroindan (193 mg, 0.3 mmol, pyridine (119 ng, 1.5 mmol) and 2 mL of dichloromethane in 15 mL of dry Schlenk tube. After dissolving the solid at room temperature, the solution of phenylthioacetyl chloride (84 ng, 0.45 mmol) in dichloromethane (2 mL) was added dropwise to the system under ice-cooling. After completion of the adding, stirring the reaction mixture for 2 hours at room temperature, the reaction was complete and analyzed by TLC detecting (petroleum ether:ethyl acetate=10:1). The organic phase was washed with saturated brine, dried over anhydrous magnesium sulfate and allowed to stand. The desiccant was removed by suction filtration, and the filtrate was removed from the solvent by rotary evaporator and the crude product was used directly in the next step.

Aluminum chloride (120 ng, 0.9 mmol), lithium aluminum hydride (34 mg, 0.9 mmol) and 3 mL of anhydrous ether were weighed in a 15 mL dry Schlenk tube under nitrogen atmosphere and was heated to 40° C. by oil bath. The reaction was reacted to reflux for 0.5 hours and then cooled to room temperature. The ether solution (3 mL) of the crude amide crude product prepared in the previous step was added dropwise to the system using a syringe. After completion of the adding, stirring the reaction mixture for 2 hours at room temperature, the reaction was complete and analyzed by TLC (TLC detection, petroleum ether:ethyl acetate=10:1). The reaction was quenched by the dropwise addition of 2 mL of water to the system under ice-water cooling bath, and the aqueous phase was extracted with ethyl acetate (3 mL×3). The organic phase was washed with saturated brine, dried over anhydrous magnesium sulfate and allowed to stand. The desiccant was removed by suction filtration, and the filtrate was removed with a rotary evaporator. The residue was purified by silica gel column chromatography (petroleum ether:ethyl acetate=30:1) to give 147 mg of white solid with 63% yield in two steps.

Mp 58-60° C., $[\alpha]_D^{25}$ 228.8 (c 0.5, CHCl$_3$). $^1$H NMR (400 MHz, CDCl$_3$) δ 7.30-7.24 (m, 3H), 7.23-7.13 (m, 6H), 7.09 (t, J=7.8 Hz, 2H), 6.93 (dd, J=8.0, 1.6 Hz, 2H), 6.72 (dd, J=7.6, 1.6 Hz, 2H), 6.66 (d, J=7.3 Hz, 1H), 6.09 (d, J=7.9 Hz, 1H), 3.40 (t, J=5.4 Hz, 1H), 3.12-2.66 (m, 7H), 2.66-2.55 (m, 1H), 2.38 (dd, J=22.0, 11.0 Hz, 1H), 2.21-2.05 (m, 3H), 1.19 (s, 18H), 1.15 (s, 18H); $^{31}$P NMR (162 MHz, CDCl$_3$) δ −18.9 (s). $^{13}$C NMR (101 MHz, CDCl$_3$) δ 152.6 (d, J=24.5 Hz), 150.0 (d, J=6.8 Hz), 149.9 (d, J=6.0 Hz), 144.7 (d, J=2.6 Hz), 144.1 (d, J=7.3 Hz), 143.8 (d, J=3.4 Hz), 138.5 (d, J=11.9 Hz), 136.4 (d, J=13.3 Hz), 135.8, 135.2, 135.0, 134.0 (d, J=1.9 Hz), 130.1, 129.0, 128.4 (d, J=7.0 Hz), 128.1 (d, J=9.5 Hz), 127.8, 127.1, 126.4, 125.9, 122.4, 121.5, 113.8, 108.0, 61.7 (d, J=3.4 Hz), 41.9, 39.0 (d, J=3.7 Hz), 36.1, 34.9, 34.8, 33.9, 31.6, 31.5, 31.3, 31.0. HRMS (MALDI) Calcd for C$_{53}$H$_{67}$NPS [M+H]$^+$: 780.4726; Found: 780.4724.

(In the following Examples, Compounds Ib-Io were prepared via the same processes as Example 1 except of the reactants changed corresponding).

Example 2

Synthesis of (R)-7'-(bis(2,6-dimethylphenyl)phosphino)-N-(2-(phenylthio)ethyl)-2,2',3,3'-tetrahydro-1,1'-spirobi[inden]-7-amine (Ib)

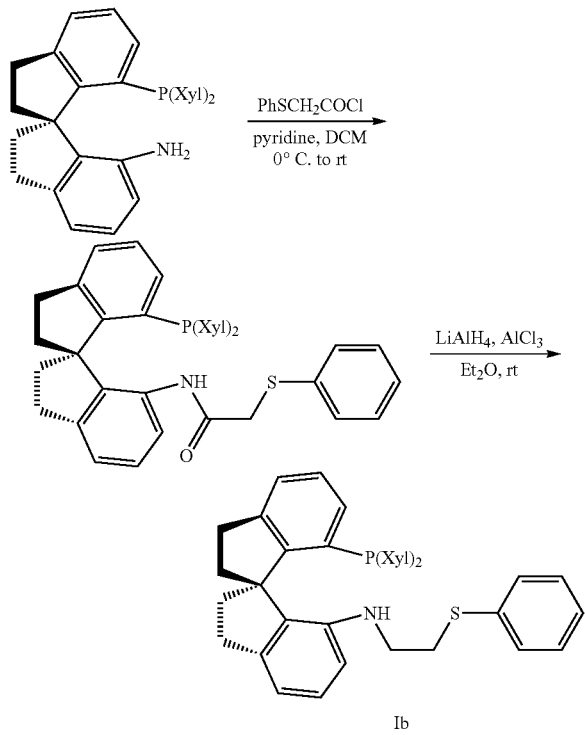

Specific process can be found in Example 1, white solid, yield: 65%.

Mp 58-60° C., $[\alpha]_D^{25}$ 277.0 (c 0.5, CHCl$_3$). $^1$H NMR (400 MHz, CDCl$_3$) δ 7.28-7.08 (m, 8H), 7.03 (t, J=7.6 Hz, 1H), 6.84 (s, 1H), 6.81 (s, 1H), 6.72-6.63 (m, 3H), 6.58 (d, J=7.1 Hz, 2H), 5.92 (d, J=7.9 Hz, 1H), 3.17-3.11 (m, 1H), 3.08-2.96 (m, 4H), 2.78 (td, J=12.9, 6.5 Hz, 1H), 2.68-2.53 (m, 2H), 2.53-2.43 (m, 1H), 2.43-2.33 (m, 2H), 2.33-2.23 (m, 1H), 2.17 (s, 6H), 2.16 (s, 6H); $^{31}$P NMR (162 MHz, CDCl$_3$) δ −22.6 (s); $^{13}$C NMR (101 MHz, CDCl$_3$) δ 153.1 (d, J=25.3 Hz), 144.6 (d, J=2.8 Hz), 144.1 (d, J=7.7 Hz), 143.5 (d, J=1.8 Hz), 139.5 (d, J=13.0 Hz), 137.3 (d, J=6.0 Hz), 137.1 (d, J=8.1 Hz), 136.2 (d, J=13.3 Hz), 135.8, 135.0, 134.8, 134.4 (d, J=2.9 Hz), 133.4 (d, J=3.4 Hz), 132.5, 132.2, 130.9, 130.7, 130.4, 130.1, 129.5, 129.0, 128.1, 127.5, 126.4, 126.0, 113.7, 107.9, 61.7 (d, J=3.2 Hz), 41.5, 39.9 (d, J=6.0 Hz), 36.3, 33.8, 31.5, 31.1, 21.4. HRMS (MALDI) Calcd for C$_{41}$H$_{43}$NPS [M+H]$^+$: 612.2848; Found: 612.2845.

Example 3

Synthesis of (R)-7'-(bis(3,5-di-tert-butylphenyl)phosphino)-N-(2-(phenylthio)ethyl)-2,2',3,3'-tetrahydro-1,1'-spirobi[inden]-7-amine (Ic)

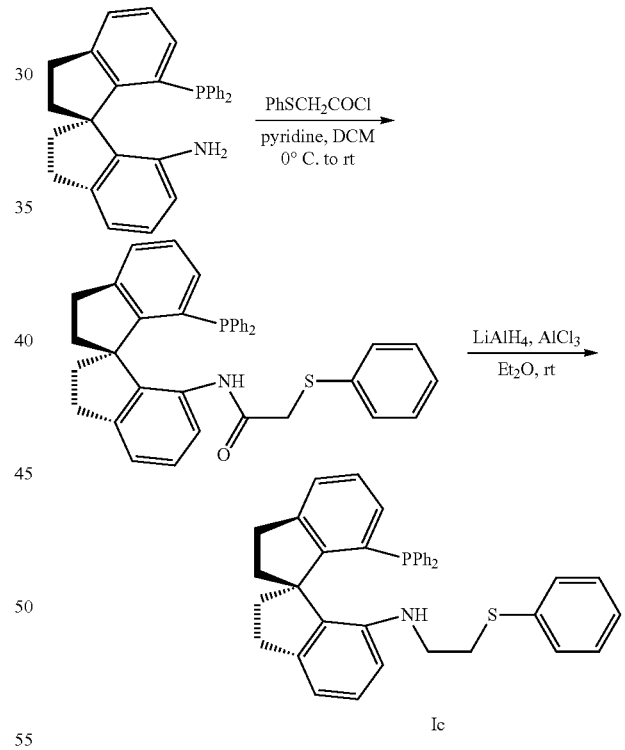

Specific process can be found in Example 1, white solid, yield: 51%.

Mp 55-58° C., $[\alpha]_D^{25}$ 245.5 (c 0.5, CHCl$_3$). $^1$H NMR (400 MHz, CDCl$_3$) δ 7.31-6.91 (m, 19H), 6.65 (d, J=7.3 Hz, 1H), 5.93 (d, J=7.9 Hz, 1H), 3.27-3.18 (m, 1H), 3.11-2.93 (m, 4H), 2.93-2.81 (m, 1H), 2.68 (t, J=6.5 Hz, 2H), 2.53-2.33 (m, 3H), 2.32-2.23 (m, 1H), 2.18-2.08 (m, 1H); $^{31}$P NMR (162 MHz, CDCl$_3$) δ −22.3 (s); $^{13}$C NMR (101 MHz, CDCl$_3$) δ 153.3 (d, J=25.3 Hz), 144.6 (d, J=3.1 Hz), 144.3 (d, J=7.8 Hz), 143.4, 139.7 (d, J=13.9 Hz), 136.8 (d, J=14.0 Hz), 135.6, 134.5 (d, J=2.5 Hz), 134.34, 134.25, 134.1, 134.0, 133.3, 133.2 (d, J=3.5 Hz), 133.1, 130.0, 129.0, 128.4 (d, J=3.6 Hz), 128.1 (d, J=5.5 Hz), 128.0 (d, J=7.3 Hz), 127.7 (d, J=9.9 Hz), 126.4, 126.3, 113.8, 108.0, 61.7 (d, J=3.2 Hz), 41.3, 40.0 (d, J=5.3 Hz), 36.2, 33.9, 31.5, 31.1. HRMS (MALDI) Calcd for $C_{37}H_{35}NPS$ [M+H]$^+$: 556.2222; Found: 556.2216.

Example 4

Synthesis of (R)-7'-(bis(3,5-di-tert-butylphenyl)phosphino)-N-(2-((2,6-dimethylphenyl)thio)ethyl)-2,2',3,3'-tetrahydro-1,1'-spirobi[inden]-7-amine (Id)

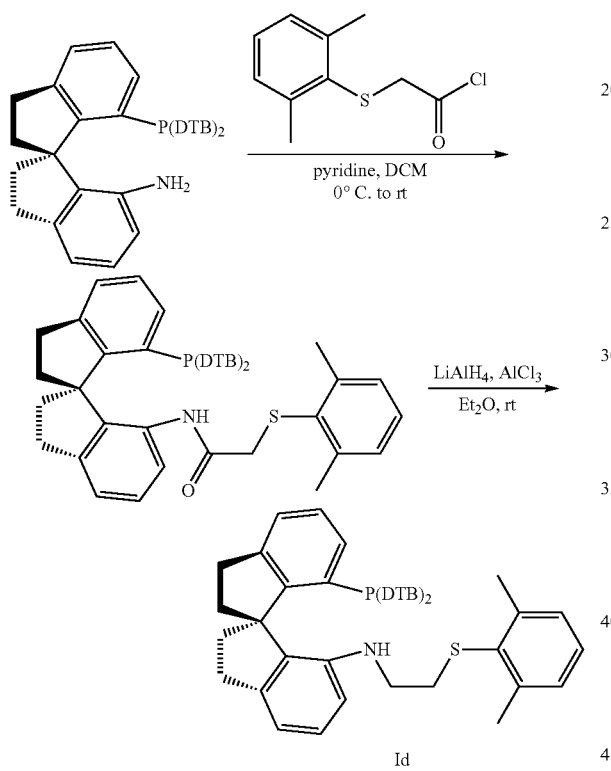

Id

Specific process can be found in Example 1, white solid, yield: 69%.

Mp 71-74° C., $[\alpha]_D^{25}$ 159.2 (c 0.5, CHCl$_3$). $^1$H NMR (400 MHz, CDCl$_3$) δ 7.31-7.27 (m, 2H), 7.23-7.16 (m, 2H), 7.12-7.02 (m, 5H), 6.94 (dd, J=8.0, 1.6 Hz, 2H), 6.73 (dd, J=7.6, 1.6 Hz, 2H), 6.66 (d, J=7.4 Hz, 1H), 6.03 (d, J=8.0 Hz, 1H), 3.42-3.35 (m, 1H), 3.13-2.87 (m, 3H), 2.86-2.72 (m, 2H), 2.55-2.44 (m, 3H), 2.39 (s, 6H), 2.20-2.06 (m, 3H), 1.20 (s, 18H), 1.16 (s, 18H); $^{31}$P NMR (162 MHz, CDCl$_3$) δ −18.8 (s); $^{13}$C NMR (101 MHz, CDCl$_3$) δ 152.6 (d, J=24.7 Hz), 150.0 (d, J=6.9 Hz), 149.9 (d, J=6.1 Hz), 144.6 (d, J=3.1 Hz), 144.1 (d, J=7.4 Hz), 143.9 (d, J=3.4 Hz), 143.3, 138.4 (d, J=11.8 Hz), 136.4 (d, J=13.5 Hz), 135.1 (d, J=23.2 Hz), 133.9 (d, J=1.7 Hz), 133.2, 132.4 (d, J=3.3 Hz), 128.4, 128.3 (d, J=6.0 Hz), 128.2, 128.1 (d, J=2.5 Hz), 127.9, 127.1, 126.0, 122.3, 121.5, 113.7, 107.8, 61.7 (d, J=3.2 Hz), 42.4, 38.9 (d, J=3.6 Hz), 36.0, 35.1, 34.9, 34.8, 31.6, 31.5, 31.3, 31.0, 22.2. HRMS (MALDI) Calcd for $C_{55}H_{71}NPS$ [M+H]$^+$: 808.5039; Found: 808.5042.

Example 5

Synthesis of (R)-7'-(bis(3,5-di-tert-butylphenyl)phosphino)-N-(2-((3,5-dimethylphenyl)thio)ethyl)-2,2',3,3'-tetrahydro-1,1'-spirobi[inden]-7-amine (Ie)

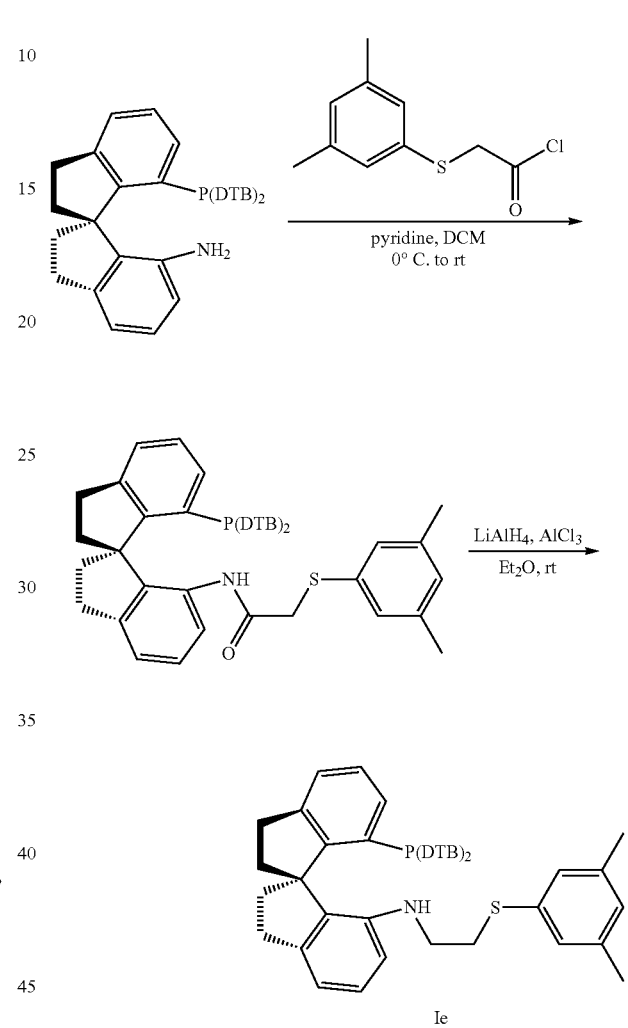

Ie

Specific process can be found in Example 1, white solid, yield: 65%.

Mp 60-62° C., $[\alpha]_D^{25}$ 229.0 (c 0.5, CHCl$_3$). $^1$H NMR (400 MHz, CDCl$_3$) δ 7.28-7.13 (m, 4H), 7.12-7.05 (m, 2H), 6.92 (d, J=8.0 Hz, 2H), 6.82 (s, 2H), 6.77 (s, 1H), 6.72 (d, J=7.5 Hz, 2H), 6.65 (d, J=7.4 Hz, 1H), 6.09 (d, J=8.0 Hz, 1H), 3.41 (t, J=5.5 Hz, 1H), 3.09-2.57 (m, 8H), 2.43-2.31 (m, 1H), 2.23 (s, 6H), 2.18-2.06 (m, 3H), 1.18 (s, 18H), 1.14 (s, 18H); $^{31}$P NMR (162 MHz, CDCl$_3$) δ −18.8 (s); $^{13}$C NMR (101 MHz, CDCl$_3$) δ 152.6 (d, J=24.5 Hz), 150.0 (d, J=6.6 Hz), 149.9 (d, J=5.9 Hz), 144.6 (d, J=2.8 Hz), 144.1 (d, J=7.4 Hz), 143.8 (d, J=3.2 Hz), 138.5, 136.3, 135.3, 134.9, 133.9, 132.6 (d, J=3.7 Hz), 128.4, 128.3 (d, J=6.6 Hz), 128.1, 127.9, 127.7, 127.1, 125.9, 123.3, 122.3, 121.5, 113.7, 107.9, 61.7 (d, J=3.0 Hz), 42.0, 39.0 (d, J=3.7 Hz), 36.0, 34.9, 34.8, 33.7, 31.6, 31.5, 31.3, 30.9, 21.3. HRMS (MALDI) Calcd for $C_{55}H_{71}NPS$ [M+H]$^+$: 808.5039; Found: 808.5039.

Example 6

Synthesis of (R)-7'-(bis(3,5-di-tert-butylphenyl)phosphino)-N-(2-(p-tolylthio)ethyl)-2,2',3,3'-tetrahydro-1,1'-spirobi[inden]-7-amine (If)

Example 7

Synthesis of (R)-7'-(bis(3,5-di-tert-butylphenyl)phosphino)-N-(2-(naphthalen-2-ylthio)ethyl)-2,2',3,3'-tetrahydro-1,1'-spirobi[inden]-7-amine (Ig)

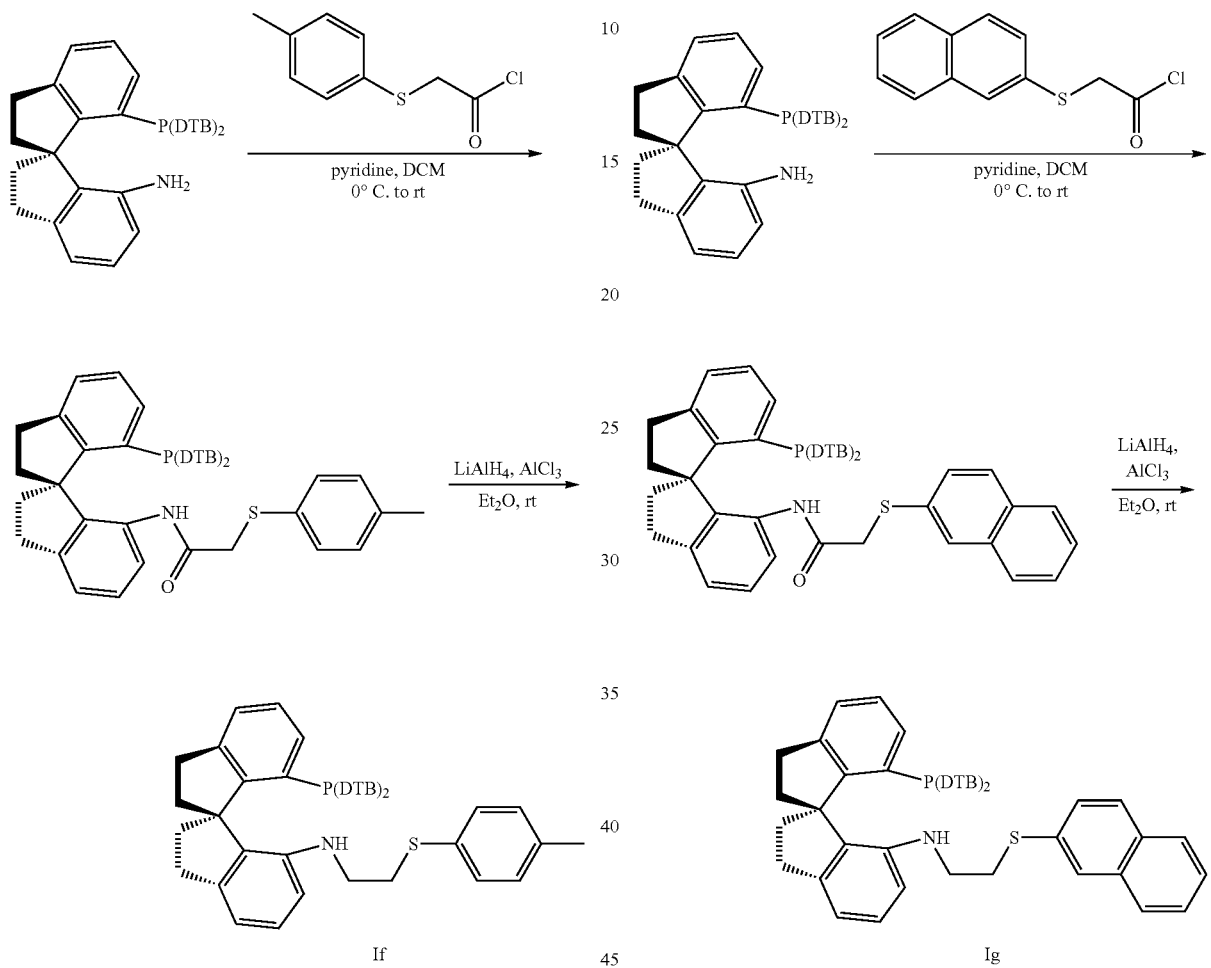

Specific process can be found in Example 1, white solid, yield: 70%.

Mp 60-62° C. $[\alpha]_D^{25}$ 236.1 (c 0.5, CHCl$_3$). $^1$H NMR (400 MHz, CDCl$_3$) δ 7.29-7.14 (m, 4H), 7.13-6.99 (m, 6H), 6.92 (d, J=8.0 Hz, 2H), 6.72 (d, J=7.5 Hz, 2H), 6.65 (d, J=7.3 Hz, 1H), 6.06 (d, J=7.9 Hz, 1H), 3.40 (t, J=5.3 Hz, 1H), 3.09-2.53 (m, 8H), 2.44-2.33 (m, 1H), 2.28 (s, 3H), 2.17-2.06 (m, 3H), 1.18 (s, 18H), 1.14 (s, 18H); $^{31}$P NMR (162 MHz, CDCl$_3$) δ −18.9 (s); $^{13}$C NMR (101 MHz, CDCl$_3$) δ 152.5 (d, J=25.0 Hz), 149.6 (d, J=6.5 Hz), 149.8 (d, J=5.9 Hz), 144.5 (d, J=2.3 Hz), 143.9 (d, J=7.7 Hz), 143.7 (d, J=3.2 Hz), 138.3 (d, J=11.4 Hz), 137.2, 136.5, 136.3 (d, J=13.1 Hz), 135.1, 134.9, 133.8 (d, J=1.8 Hz), 132.5 (d, J=3.8 Hz), 131.7, 131.0, 129.6, 129.2, 128.3 (d, J=6.8 Hz), 128.0 (d, J=5.8 Hz), 127.8, 127.0, 125.8, 122.2, 121.4, 113.6, 107.8, 61.6 (d, J=3.3 Hz), 41.7, 38.9 (d, J=4.3 Hz), 36.0, 34.8, 34.7, 34.5, 31.5, 31.3, 31.2, 30.8, 21.0. HRMS (MALDI) Calcd for CH$_{69}$NPS [M+H]$^+$: 794.4883; Found: 794.4886.

Specific process can be found in Example 1, white solid, yield:

Mp 69-71° C., $[\alpha]_D^{25}$ 188.1 (c 0.5, CHCl$_3$). $^1$H NMR (400 MHz, CDCl$_3$) δ 7.75 (d, J=7.6 Hz, 1H), 7.66 (t, J=8.5 Hz, 2H), 7.60 (s, 1H), 7.48-7.37 (m, 2H), 7.31-7.05 (m, 7H), 6.93 (d, J=8.0 Hz, 2H), 6.72 (d, J=7.5 Hz, 2H), 6.66 (d, J=7.3 Hz 1H), 6.11 (d, J=7.9 Hz, 1H), 3.51-3.41 (m, 1H), 3.09-2.75 (m, 7H), 2.72-2.60 (m, 1H), 2.46-2.32 (m, 1H), 2.20-2.04 (m, 3H), 1.15 (s, 18H), 1.14 (s, 18H); $^{31}$P NMR (162 MHz, CDCl$_3$) δ −18.82 (s); $^{13}$C NMR (101 MHz, CDCl$_3$) δ 152.6 (d, J=24.5 Hz), 150.0 (d, J=6.9 Hz), 149.9 (d, J=6.1 Hz), 144.7 (d, J=2.3 Hz), 144.1 (d, J=7.5 Hz), 143.8 (d, J=3.1 Hz), 138.5 (d, J=11.8 Hz), 136.3 (d, J=13.1 Hz), 135.1 (d, J=22.9 Hz), 134.0, 133.8, 133.4, 132.7 (d, J=3.3 Hz), 132.0, 128.44, 128.36, 128.1 (d, J=9.6 Hz), 128.0, 127.9, 127.8, 127.2, 127.1, 126.6, 126.0, 125.8, 122.4, 121.5, 113.9, 108.0, 61.7 (d, J=3.2 Hz), 42.0, 39.0 (d, J=4.0 Hz), 36.1, 34.9, 34.8, 33.8, 31.6, 31.5, 31.3, 30.9. HRMS (ESI) Calcd for C$_{57}$H$_{69}$NPS [M+H]$^+$: 830.4883; Found: 830.4885.

Example 8

Synthesis of (R)-7'-(bis(3,5-di-tert-butylphenyl)phosphino)-N-(2-((4-methoxyphenyl)thio)ethyl)-2,2',3,3'-tetrahydro-1,1'-spirobi[inden]-7-amine (Ih)

Example 9

Synthesis of (R)-7'-(bis(3,5-di-tert-butylphenyl)phosphino)-N-(2-((2,6-dichlorophenyl)thio)ethyl)-2,2',3,3'-tetrahydro-1,1'-spirobi[inden]-7-amine (Ii)

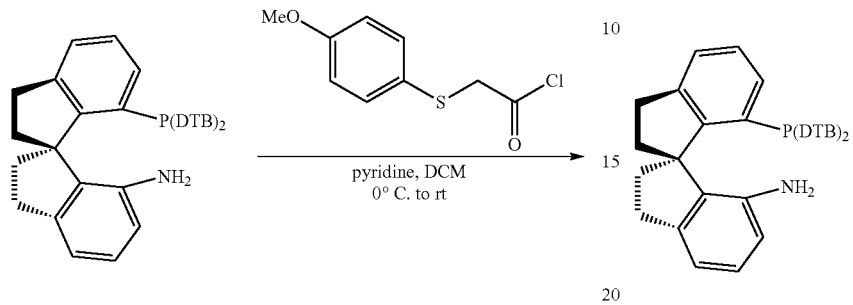
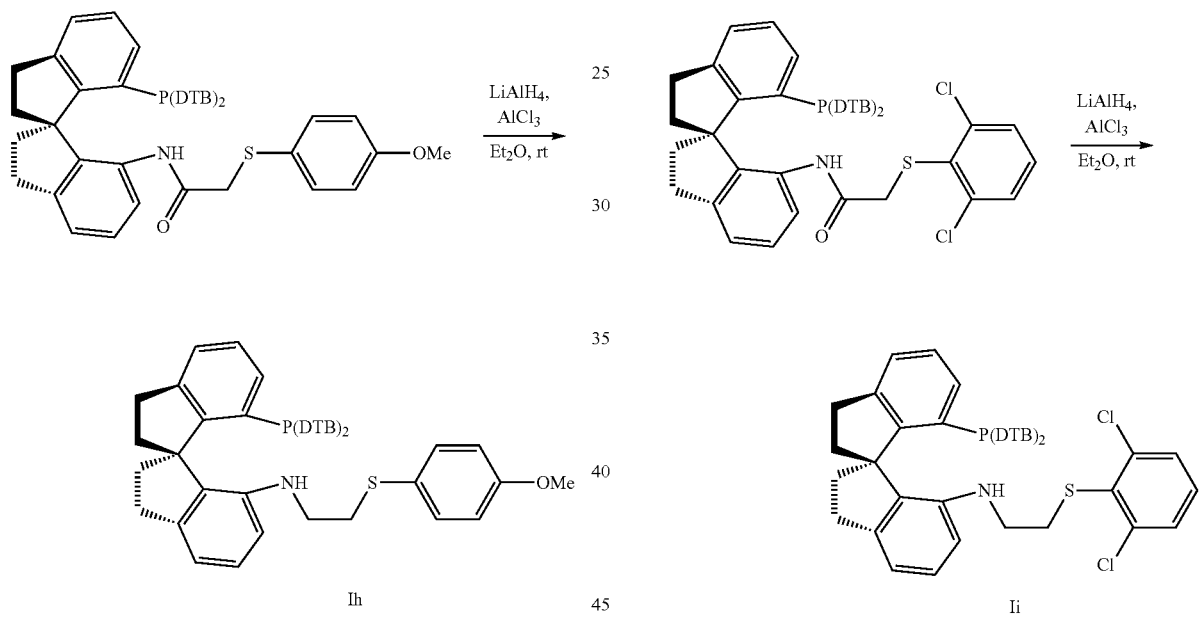

Specific process can be found in Example 1, white solid. yield: 70%.

Mp 124-126° C., $[\alpha]_D^{25}$ 194.8 (c 0.5, CHCl$_3$) $^1$H NMR (400 MHz, CDCl$_3$) δ 7.32-7.27 (m, 2H), 7.24-7.15 (m, 4H), 7.14-7.05 (m, 2H), 6.92 (d, J=8.0 Hz, 2H), 6.80-6.70 (m, 4H), 6.66 (d, J=7.3 Hz, 1H), 6.06 (d, J=7.9 Hz, 1H), 3.78 (s, 3H), 3.44-3.37 (m, 1H), 3.12-2.74 (m, 5H), 2.72-2.53 (min, 3H), 2.41 (dd, J=22.1, 10.8 Hz, 1H), 2.22-2.08 (m, 3H), 1.19 (s, 18H), 1.16 (s, 18H). $^{31}$P NMR (162 MHz, CDCl$_3$) δ −18.78 (s). $^{13}$C NMR (101 MHz, CDCl$_3$) δ 159.2, 152.6 (d, J=24.5 Hz), 150.0 (d, J=4.4 Hz), 149.9 (d, J=3.6 Hz), 144.6 (d, J=2.7 Hz), 144.1 (d, J=7.4 Hz), 143.8 (d, J=3.1 Hz), 138.4 (d, J=11.9 Hz), 136.5 (d, J=13.3 Hz), 135.2 (d, J=23.5 Hz), 134.1 (s), 133.9 (d, J=2.3 Hz), 132.5 (d, J=3.5 Hz), 128.4 (d, J=9.5 Hz), 128.1, 127.9, 127.1, 125.9, 125.6, 122.3, 121.5, 114.6, 113.7, 107.8, 61.7 (d, J=3.4 Hz), 55.4, 41.7, 38.98 (d, J=3.9 Hz), 36.2, 35.8, 34.9, 34.8, 31.6, 31.5, 31.3, 31.0. HRMS (MALDI) Calcd for C$_{54}$H$_{69}$NOPS [M+H]$^+$: 810.4832; Found: 810.4836.

Specific process can be found in Example 1, white solid yield:

Mp 78-80° C., $[\alpha]_D^{25}$ 134.7 (c 0.5, CHCl$_3$). $^1$H NMR (400 MHz, CDCl$_3$) δ 7.36-7.27 (m, 4H), 7.24-7.18 (m, 2H), 7.17-7.07 (m, 3H), 6.97 (dd, J=8.0, 1.1 Hz, 2H), 6.75 (dd, J=7.5, 1.1 Hz, 2H), 6.68 (d, J=7.3 Hz, 1H), 6.07 (d, J=8.0 Hz, 1H), 3.60 (t, J=5.6 Hz, 1H), 3.14-3.04 (m, 2H), 3.03-2.90 (m, 1H), 2.90-2.66 (m, 4H), 2.53-2.41 (m, 2H), 2.27-2.11 (m, 3H), 1.20 (s, 18H), 1.17 (s, 18H); $^{31}$P NMR (162 MHz, CDCl$_3$) δ −19.0 (s); $^{13}$C NMR (101 MHz, CDCl$_3$) δ 152.7 (d, J=25.0 Hz), 150.0 (d, J=3.8 Hz), 149.9 (d, J=3.0 Hz), 144.7 (d, J=2.6 Hz), 144.1 (d, J=7.6 Hz), 143.4 (d, J=3.4 Hz), 141.9, 138.6 (d, J=12.0 Hz), 136.5 (d, J=13.2 Hz), 135.0 (d, J=23.0 Hz), 134.1 (d, J=2.5 Hz), 132.8, 130.0, 128.6, 128.3 (d, J=3.3 Hz), 128.0 (d, J=10.6 Hz), 127.8, 127.1, 126.1, 122.2, 121.4, 113.7, 107.6, 61.7 (d, J=3.3 Hz), 41.8, 39.1 (d, J=3.9 Hz), 35.9, 35.2, 34.9, 34.8, 31.6, 31.5, 31.3, 31.0. HRMS (ESI) Calcd for C$_{53}$H$_{65}$Cl$_2$NPS [M+H]$^+$: 848.3947; Found: 848.3928.

Example 10

Synthesis of (R)-7'-(bis(3,5-di-tert-butylphenyl)phosphino)-N-(2-((4-chlorophenyl)thio)ethyl)-2,2',3,3'-tetrahydro-1,1'-spirobi[inden]-7-amine (Ij)

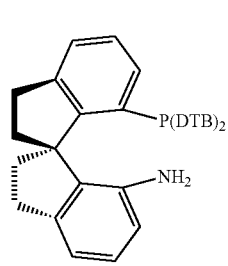
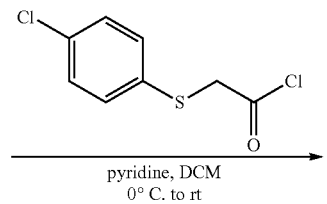
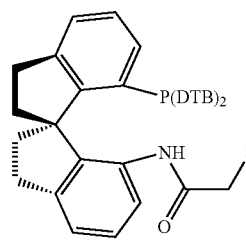
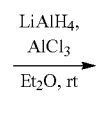
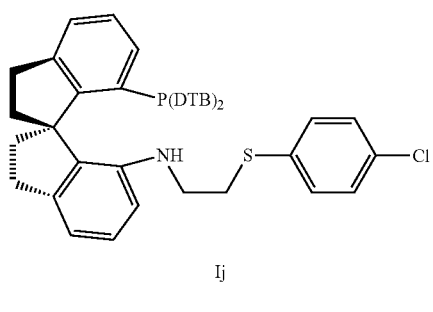

Specific process can be found in Example 1, white solid, yield:

Mp 129-131° C., $[\alpha]_D^{25}$ 240.3 (c 0.5, CHCl$_3$). $^1$H NMR (400 MHz, CDCl$_3$) δ 7.30-7.13 (m, 6H), 7.12-7.06 (m, 4H), 6.92 (dd, J=8.0, 1.3 Hz, 2H), 6.71 (dd, J=7.5, 1.3 Hz, 2H), 6.67 (d, J=7.4 Hz, 1H), 6.08 (d, J=7.9 Hz, 1H), 3.39 (t, J=5.5 Hz, 1H), 3.10-2.64 (m, 7H), 2.63-2.52 (m, 1H), 2.42-2.30 (m, 1H), 2.19-2.06 (m, 3H), 1.18 (s, 18H), 1.14 (s, 18H); $^{31}$P NMR (162 MHz, CDCl$_3$) δ −18.9 (s); $^{13}$C NMR (101 MHz, CDCl$_3$) δ 152.6 (d, J=24.5 Hz), 150.1 (d, J=7.0 Hz), 150.0 (d, J=6.0 Hz), 144.7 (d, J=3.0 Hz), 144.1 (d, J=7.4 Hz), 143.7 (d, J=3.2 Hz), 138.4 (d, J=11.7 Hz), 136.3 (d, J=13.5 Hz), 135.1 (d, J=23.6 Hz), 134.3, 134.0, 132.7 (d, J=3.7 Hz), 132.4, 131.6, 129.1, 128.6, 128.4 (d, J=3.9 Hz), 128.1 (d, J=16.4 Hz), 127.8, 127.1, 125.9, 122.4, 121.5, 114.0, 107.9, 61.7 (d, J=3.2 Hz), 41.8, 39.0 (d, J=4.0 Hz), 36.1, 34.94, 34.85, 34.2, 31.6, 31.5, 31.3, 31.0. HRMS (ESI) Calcd for C$_{53}$H$_{66}$ClNPS [M+H]$^+$: 814.4337; Found: 814.4331.

Example 11

Synthesis of (R)-7'-(bis(3,5-di-tert-butylphenyl)phosphino)-N-(2-((4-(trifluoromethyl)phenyl)thio)ethyl)-2,2',3,3'-tetrahydro-1,1'-spirobi[inden]-7-amine (Ik)

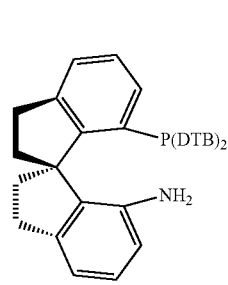
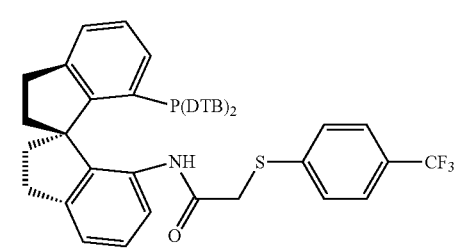
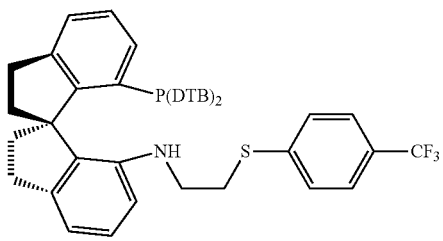

Specific process can be found in Example 1, white solid, yield:

Mp 96-98° C., $[\alpha]_D^{25}$ 376.1 (c 0.5, CHCl$_3$). $^1$H NMR (400 MHz, CDCl$_3$) δ 7.43 (d, J=8.1 Hz, 2H), 7.29-7.08 (m, 9H), 6.93 (d, J=8.0 Hz, 2H), 6.73-6.65 (m, 3H), 6.11 (d, J=7.9 Hz, 1H), 3.44-3.36 (m, 1H), 3.11-2.74 (m, 7H), 2.67-2.56 (m, 1H), 2.39-2.27 (m, 1H), 2.20-2.05 (m, 3H), 1.18 (s, 18H), 1.14 (s, 18H); $^{31}$P NMR (162 MHz, CDCl$_3$) δ −19.0 (s); $^{13}$C NMR (101 MHz, CDCl$_3$) δ 152.6 (d, J=24.8 Hz), 150.1 (d, J=7.1 Hz), 150.0 (d, J=5.8 Hz), 144.8 (d, J=2.5 Hz), 144.1 (d, J=7.5 Hz), 143.7 (d, J=3.4 Hz), 141.7, 138.4 (d, J=11.9 Hz), 136.2 (d, J=12.9 Hz), 135.1 (d, J=23.3 Hz), 134.0 (d, J=1.9 Hz), 132.7 (d, J=3.2 Hz), 128.4 (d, J=2.9 Hz), 128.2, 127.9 (d, J=19.7 Hz), 127.2, 125.9, 125.7 (d, J=3.7 Hz), 122.5, 121.5, 114.2, 108.0, 61.7 (d, J=3.3 Hz), 41.9, 38.9 (d, J=3.9 Hz), 36.0, 34.94, 34.84, 32.8, 31.6, 31.4, 31.3, 30.9; HRMS (ESI) Calcd for C$_{54}$H$_{66}$F$_3$NPS [M+H]$^+$: 848.4600; Found: 848.4605.

Example 12

Synthesis of (R)-7'-(bis(3,5-di-text-butylphenyl)phosphino)-N-(2-(ethylthio)ethyl)-2,2',3,3'-tetrahydro-1,1'-spirobi[inden]-7-amine (If)

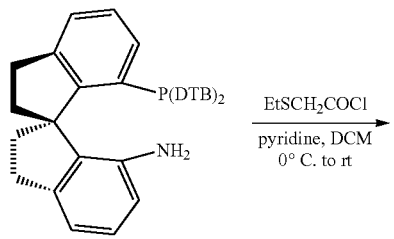

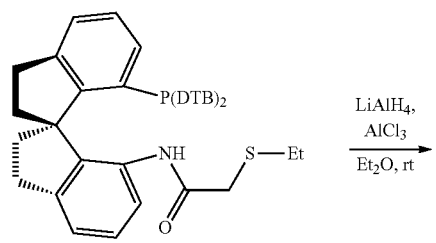

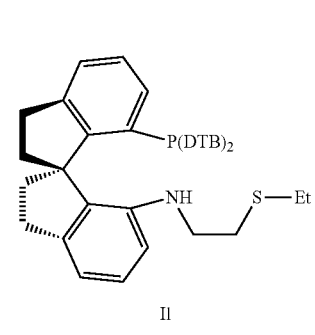

If

Specific process can be found in Example 1, white solid, yield:

Mp 94-96° C., $[\alpha]_D^{25}$ 172.3 (c 0.5, CHCl$_3$). $^1$H NMR (400 MHz, CDCl$_3$) δ 7.33-7.24 (m, 2H), 7.23-7.06 (m, 4H), 6.94 (d, J=7.9 Hz, 2H), 6.72 (d, J=7.5 Hz, 2H), 6.67 (d, J=7.3 Hz, 1H), 6.16 (d, J=7.9 Hz, 1H), 3.43-3.33 (m, 1H), 3.13-2.72 (m, 5H), 2.68-2.55 (m, 1H), 2.46-2.25 (m, 5H), 2.21-2.05 (m, 3H), 1.22 (s, 18H), 1.17-1.08 (m, 21H); $^{31}$P NMR (162 MHz, CDCl$_3$) δ −18.8 (s); $^{13}$C NMR (101 MHz, CDCl$_3$) δ 152.6 (d, J=24.7 Hz), 150.0 (d, J=7.2 Hz), 149.9 (d, J=6.1 Hz), 144.6 (d, J=2.5 Hz), 144.2 (d, J=3.1 Hz), 144.1 (d, J=7.2 Hz), 138.4 (d, J=11.5 Hz), 136.4 (d, J=13.5 Hz), 135.2, 134.9, 133.9, 132.5 (d, J=3.6 Hz), 128.4 (d, J=2.7 Hz), 128.1 (d, J=10.5 Hz), 127.9, 127.1, 125.9, 122.3, 121.5, 113.8, 108.0, 61.7 (d, J=3.2 Hz), 42.8, 38.9 (d, J=3.9 Hz), 36.0, 35.0, 34.8, 31.6, 31.5, 31.4, 31.3, 30.9, 25.9, 15.0. HRMS (ESI) Calcd for C$_{49}$H$_{67}$NPS [M+H]$^+$: 732.4726; Found: 732.4728.

Example 13

Synthesis of (R)-7'-(bis(3,5-di-tert-butylphenyl)phosphino)-N-(2-(tert-butylthio)ethyl)-2,2',3,3'-tetrahydro-1,1'-spirobi[inden]-7-amine (Im)

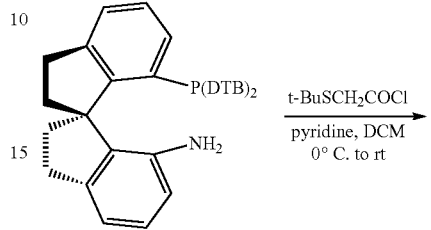

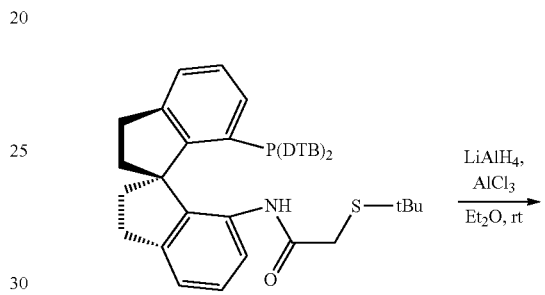

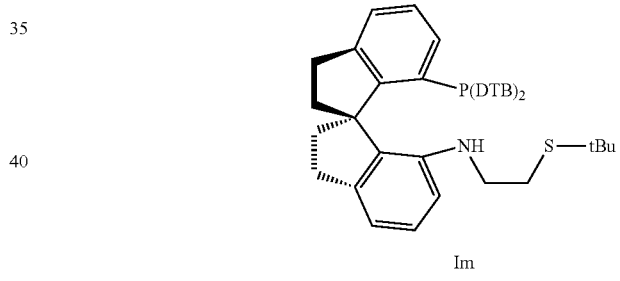

Im

Specific process can be found in Example 1, white solid, yield: 76%.

Mp 152-155° C., $[\alpha]_D^{25}$ 196.5 (c 0.5, CHCl$_3$). $^1$H NMR (400 MHz, CDCl$_3$) δ 7.31-7.24 (m, 2H), 7.24-7.07 (m, 4H), 6.96-6.90 (m, 2H), 6.78-6.71 (m, 2H), 6.66 (d, J=7.3 Hz, 1H), 6.16 (d, J=7.9 Hz, 1H), 3.50-3.40 (m, 1H), 3.14-2.98 (m, 2H), 2.95-2.83 (m, 2H), 2.81-2.70 (m, 1H), 2.65-2.54 (m, 1H), 2.47-2.37 (m, 3H), 2.20-2.02 (m, 3H), 1.22 (s, 18H), 1.19 (s, 9H), 1.16 (s, 18H); $^{31}$P NMR (162 MHz, CDCl$_3$) δ −18.4 (s); $^{13}$C NMR (101 MHz, CDCl$_3$) δ 152.6 (d, J=24.8 Hz), 149.94 (d, J=3.4 Hz), 149.88 (d, J=3.0 Hz), 144.6 (d, J=2.2 Hz), 144.3 (d, J=3.4 Hz), 144.0 (d, J=7.5 Hz), 138.3 (d, J=11.8 Hz), 136.4 (d, J=13.0 Hz), 135.0 (d, J=23.5 Hz), 133.8 (s), 132.3 (d, J=3.3 Hz), 128.4 (s), 128.3 (d, J=11.0 Hz), 128.1 (d, J=9.9 Hz), 127.1 (s), 125.9 (s), 122.2 (s), 121.5 (s), 113.7 (s), 108.0 (s), 61.7 (d, J=3.1 Hz), 42.7 (s), 41.8 (s), 38.85 (d, J=3.6 Hz), 35.92 (s), 34.94 (s), 34.8 (s), 31.6 (s), 31.5 (s), 31.3 (s), 31.1 (s), 30.9 (s), 28.5 (s). HRMS (MALDI) Calcd for C$_{51}$H$_{71}$NPS [M+H]$^+$: 760.5039; Found: 760.5036.

Example 14

Synthesis of (R)-7'-(bis(3,5-di-tert-butylphenyl)phosphino)-N-(2-(cyclohexylthio)ethyl)-2,2',3,3'-tetrahydro-1,1'-spirobi[inden]-7-amine (In)

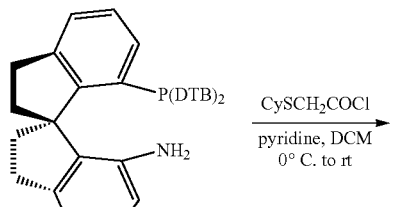

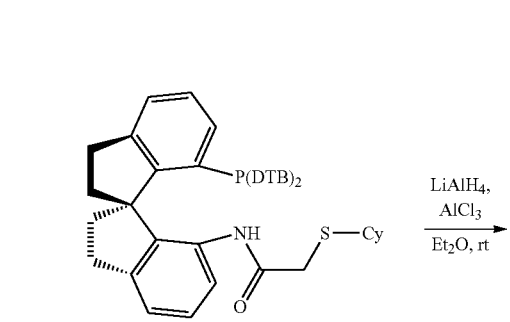

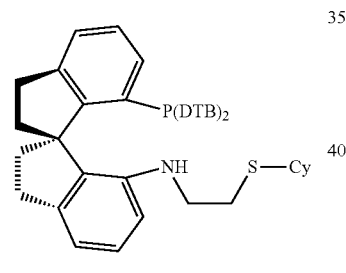

In

Specific process can be found in Example 1, colorless oily liquid, yield: 45%.

Mp [α]$_D^{25}$ 186.8 (c 0.5, CHCl$_3$). $^1$H NMR (400 MHz, CDCl$_3$) δ 7.31-7.25 (m, 2H), 7.23-7.05 (m, 4H), 6.93 (dd, J=8.0, 1.8 Hz, 2H), 6.73 (dd, J=7.5, 1.8 Hz, 2H), 6.66 (d, J=7.4 Hz, 1H), 6.14 (d, J=7.9 Hz, 1H), 3.39 (t, J=5.4 Hz 1H), 3.11-2.73 (m, 5H), 2.66-2.56 (m, 1H), 2.48-2.27 (m, 4H), 2.19-2.05 (m, 3H), 1.85-1.77 (m, 2H), 1.75-1.66 (m, 2H), 1.62-1.55 (m, 1H), 1.23-1.13 (m, 41H). $^{31}$P NMR (162 MHz, CDCl$_3$) δ -18.72 (s). $^{13}$C NMR (101 MHz, CDCl$_3$) δ 152.6 (d, J=24.5 Hz), 149.97 (d, J=4.3 Hz), 149.91 (d, J=3.7 Hz), 144.6 (d, J=2.6 Hz), 144.2 (d, J=3.2 Hz), 143.9 (d, J=7.3 Hz), 138.4 (d, J=11.9 Hz), 136.5 (d, J=13.4 Hz), 135.1 (d, J=23.5 Hz), 133.8 (d, J=2.3 Hz), 132.5 (d, J=3.5 Hz), 128.4 (d, J=11.1 Hz), 128.1 (d, J=3.9 Hz), 127.9 (s), 127.0, 125.9, 122.2, 121.5, 113.7, 108.0, 61.7 (d, J=3.3 Hz), 43.3, 42.9, 38.9 (d, J=3.8 Hz), 36.1, 34.9, 34.8, 33.9, 31.6, 31.5, 31.3, 31.0, 30.0, 26.1, 25.9. HRMS (MALDI) Calcd for C$_{53}$H$_{73}$NPS [M+H]$^+$: 786.5196; Found: 786.5198.

Example 15

Synthesis of (R)—N-(2-(benzylthio)ethyl)-7'-(bis(3,5-di-tert-butylphenyl)phosphino)-2,2',3,3'-tetrahydro-1,1'-spirobi[inden]-7-amine (Io)

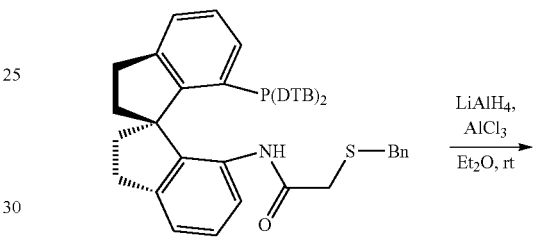

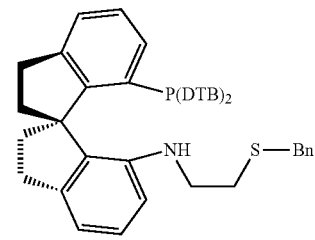

Io

Specific process can be found in Example 1, white solid, yield: 70%.

Mp 47-49° C., [α]$_D^{25}$ 168.8 (c 0.5, CHCl$_3$). $^1$H NMR (400 MHz, CDCl$_3$) δ 7.32-7.07 (m, 11H), 6.94 (d, J=8.0 Hz, 2H), 6.73 (d, J=7.5 Hz, 2H), 6.67 (d, J=7.4 Hz, 1H), 6.11 (d, J=7.9 Hz, 1H), 3.52 (d, J=13.4 Hz, 1H), 3.47 (d, J=13.5 Hz, 1H), 3.36 (t, J=5.2 Hz, 1H), 3.14-2.72 (m, 5H), 2.58 (td, J=11.8, 6.0 Hz, 1H), 2.47-2.28 (m, 2H), 2.28-2.07 (m, 4H), 1.21 (s, 18H), 1.16 (s, 18H); $^{31}$P NMR (162 MHz, CDCl$_3$) δ -18.8; $^{13}$C NMR (101 MHz, CDCl$_3$) δ 152.6 (d, J=24.5 Hz), 150.0 (d, J=7.5 Hz), 149.9 (d, J=6.9 Hz), 144.6 (d, J=2.8 Hz), 144.1 (d, J=3.9 Hz), 144.0, 138.5, 138.4 (d, J=3.3 Hz), 136.5, 136.4, 135.2, 135.0, 133.9 (d, J=1.9 Hz), 132.6 (d, J=3.5 Hz), 128.9, 128.6, 128.4 (d, J=3.7 Hz), 128.1 (d, J=8.5 Hz), 127.9, 127.1 (d, J=5.7 Hz), 125.9, 122.3, 121.5, 61.7 (d, J=3.2 Hz), 42.4, 38.9 (d, J=4.0 Hz), 36.2 (d, J=17.2 Hz), 34.9 (d, J=10.5 Hz), 31.6, 31.5, 31.3, 31.0, 29.9. HRMS (MALDI) Calcd for C$_{54}$H$_{69}$NPS [M+H]$^+$: 794.4883; Found: 794.4885.

Example 16

Synthesis of (R)—N-((1,3-dithian-2-yl)methyl)-7'-(bis(3,5-di-tert-butylphenyl)phosphino)-2,2',3,3'-tetrahydro-1,1'-spirobi[inden]-7-anine (IIa)

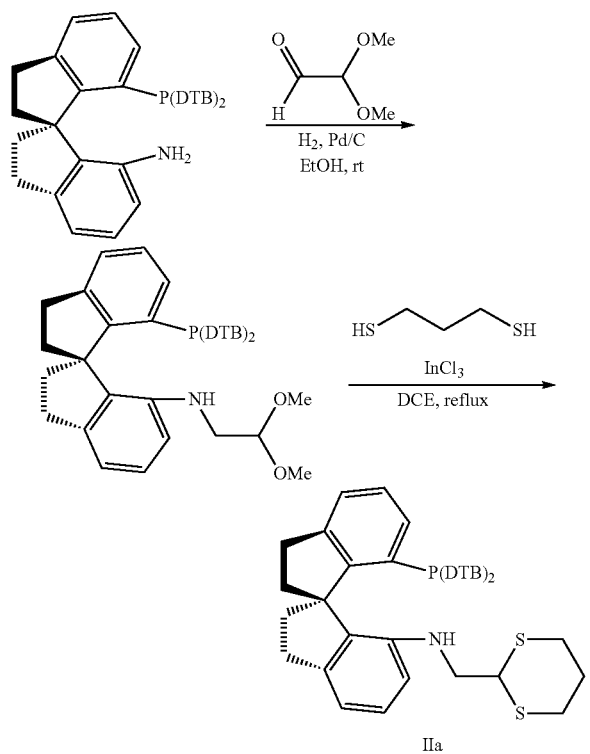

To a dry and clean 15 mL Schlenk tube equipped with magnetic stirring, was added (R)-7-di-(3,5-di-tert-butylphenyl) phosphino-7'-amino-1,1'-spiroindane (193 mg, 0.3 mmol) and 10% palladium(30 mL %, 58 mg). the system was replaced with argon atmosphere, and anhydrous ethanol (3 mL) and aqueous glyoxal dimethyl acetal (60% aq., 0.66 mL, 3.0 mmol) were adding sequencely and stirred well. The system quickly replaced with hydrogen atmosphere, the reaction mixture was reacted for 4 hours at room temperature, the reaction was reacted complete and analyzed by TLC detecting. The reaction system was filtered through celite to remove palladium carbon. The filtrate was removed with a rotary evaporator. The residue was diluted with 5 mL of ethyl acetate, washed with saturated brine, dried over anhydrous magnesium sulfate and allowed to stand. The solvent was removed by filtration and the filtrate was removed from the solvent by rotary evaporator. The crude product was used directly in the next step to replace the reaction.

The crude product obtained above was added to a dry 15 mL Schlenk tube equipped with a magnetic stirrer in a nitrogen atmosphere, indium trichloride (139 mg, 0.63 mmol), 1,3-propanedithiol (39 mg, 0.36 mmol) and 3 mL of 1,2-dichloroethane. The solution was heated to 85° C. by oil bath for 2 hours and the reaction was reacted complete and analyzed by TLC detecting. The reaction mixture was cooled to room temperature, quenched with 10% aqueous sodium hydroxide solution (2 mL). The aqueous phase was extracted with dichloromethane (3 mL×3). The organic phase was washed with saturated brine, dried over anhydrous magnesium sulfate and allowed to stand. The desiccant was removed by suction filtration, and the filtrate was removed with a rotary evaporator. The residue was purified by silica gel column chromatography (petroleum ether:ethyl acetate=30:1) to give 143 mg of white solid with 65% yield.

Mp 115-118° C., $[\alpha]_D^{25}$ 179.9 (c 0.5, CHCl$_3$). $^1$H NMR (400 MHz, CDCl$_3$) δ 7.29-7.25 (m, 2H), 7.24 (t, J=1.7 Hz, 1H), 7.15 (m, 2H), 7.10-7.05 (m, 1H), 6.92 (dd, J=7.9, 1.8 Hz, 2H), 6.78 (dd, J=7.7, 1.8 Hz, 2H), 6.66 (d, J=7.3 Hz, 1H), 6.23 (d, J=7.9 Hz, 1H), 4.19 (dd, J=6.9, 4.5 Hz, 1H), 3.38-3.29 (m, 1H), 3.18 (s, 3H), 3.03 (s, 3H), 3.10-2.92 (m, 3H), 2.91-2.83 (m, 1H), 2.73-2.61 (m, 2H), 2.43-2.32 (m, 1H), 2.08 (dd, J=12.7, 7.3 Hz, 2H), 2.03-1.91 (m, 1H), 1.20 (s, 18H), 1.17 (s, 18H); $^{31}$P NMR (162 MHz, CDCl$_3$) δ −17.8 (s); $^{13}$C NMR (101 MHz, CDCl$_3$) δ 152.3 (d, J=24.4 Hz), 150.0 (d, J=2.8 Hz), 149.9 (d, J=3.1 Hz), 144.6 (d, J=2.2 Hz), 144.5 (d, J=3.6 Hz), 144.0 (d, J=7.3 Hz), 137.9 (d, J=11.3 Hz), 136.6 (d, J=13.5 Hz), 135.4, 135.1, 133.5 (d, J=1.6 Hz), 132.4 (d, J=3.2 Hz), 128.5, 128.3 (d, J=7.6 Hz), 128.2, 127.0, 125.6, 122.1, 121.7, 113.9, 108.1, 103.2, 61.7 (d, J=3.2 Hz), 54.2, 53.7, 45.1, 38.5 (d, J=3.3 Hz), 36.2, 35.0, 34.9, 31.6, 31.5, 31.3, 30.9. HRMS (MALDI) Calcd for C$_{49}$H$_{67}$NO$_2$P [M+H]$^+$: 732.4904; Found: 732.4911.

Example 17

Synthesis of (R)—N-((1,3-dithian-2-yl)methyl)-7-(diphenylphosphino)-2,2',3,3'-tetrahydro-1,1'-spirobi[inden]-7-amine (IIb)

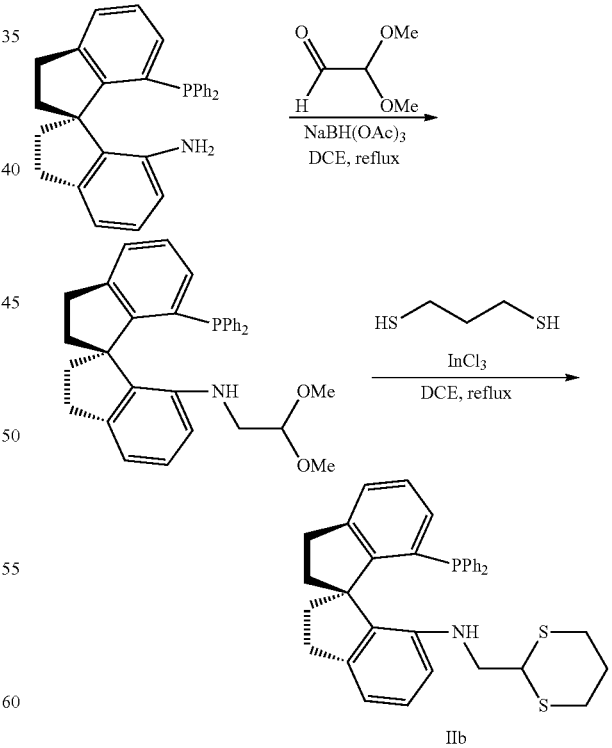

To a dry and clean Schlenk tube equipped with a magnetic stirrer, was added (R)-7-diphenylphosphino-7'-amino-1,1-spiroindan (126 mg, 0.3 mmol), sodium triacetoxyborohydride (318 mg, 1.5 mmol). The system was replaced with argon atmosphere, followed by the addition of 1,2-dichloroethane (3 mL) and glyoxal dimethyl acetal (60% aq., 0.33 mL, 1.5 mmol) in sequence and stirred well. The reaction solution was heated to 85° C. for 2 hours by oil bath and the reaction was reacted complete and analyzed by TLC detecting. The reaction mixture was cooled to room temperature, quenched with saturated aqueous sodium bicarbonate solution, the aqueous phase was extracted with dichloromethane (3 mL×3). The organic phase was washed with saturated brine, dried over anhydrous magnesium sulfate and allowed to stand. The desiccant was removed by suction filtration, and the filtrate was decanted by a rotary evaporator and the resulting crude product was used directly in the next step to replace the reaction.

To a dry 15 mL Schlenk tube equipped with a magnetic stirrer in a nitrogen atmosphere, was added the crude product obtained above, indium trichloride (139 mg, 0.63 mmol), 1,3-propanedithiol (39 mg, 0.36 mmol) and 3 mL of 1,2-dichloroethane. The reaction solution was heated to 85° C. for 2 hours by oil bath and the reaction was reacted complete and analyzed by TLC detecting. The reaction mixture was cooled to room temperature, quenched with 10% aqueous sodium hydroxide solution (2 mL). The aqueous phase was extracted with dichloromethane (3 mL×3). The organic phase was washed with saturated brine, dried over anhydrous magnesium sulfate and allowed to stand. The desiccant was removed by suction filtration, and the filtrate was removed with a rotary evaporator. The residue was purified by silica gel column chromatography (petroleum ether:ethyl acetate=10:1) to give 86 mg of white solid with 52% yield.

Mp 62-64° C., $[\alpha]_D^{25}$ 274.8 (c 0.5, CHCl$_3$). $^1$H NMR (400 MHz, CDCl$_3$) δ 7.31-6.93 (m, 15H), 6.67 (d, J=7.3 Hz, 1H), 5.98 (d, J=7.9 Hz, 1H), 3.75 (dd, J=7.4, 6.3 Hz, 1H), 3.30 (dd, J=6.6, 4.2 Hz, 1H), 3.11-2.96 (m, 5H), 2.76-2.38 (m, 7H), 2.34-2.26 (m, 1H), 2.18-2.10 (m, 1H), 2.02-1.92 (m, 1H), 1.82-1.70 (m, 1H). $^{31}$P NMR (162 MHz, CDCl$_3$) δ −22.4 (s). $^{13}$C NMR (101 MHz, CDCl$_3$) δ 153.3 (d, J=25.3 Hz), 144.6 (d, J=3.0 Hz), 144.4 (d, J=7.9 Hz), 142.7 (d, J=1.7 Hz), 139.8 (d, J=13.5 Hz), 136.8 (d, J=14.0 Hz), 134.5, 134.3, 134.1, 133.9, 133.4 (d, J=3.4 Hz), 133.1, 133.0, 128.4 (d, J=4.3 Hz), 128.1, 128.0, 128.0, 127.6 (d, J=8.7 Hz), 113.8, 107.9, 61.6 (d, J=3.1 Hz), 46.1, 45.3, 40.2 (d, J=5.3 Hz), 36.2, 31.5, 31.0, 28.6, 28.4, 25.9. HRMS (MALDI) Calcd for C$_{34}$H$_{35}$NPS$_2$ [M+H]$^+$: 552.1943; Found: 552.1945.

Example 18

Application of Chiral Spiro Phosphine-Nitrogen-Sulfur Tridentate Ligand in the Asymmetric Catalytic Hydrogenation Reaction of Carbonyl Compounds

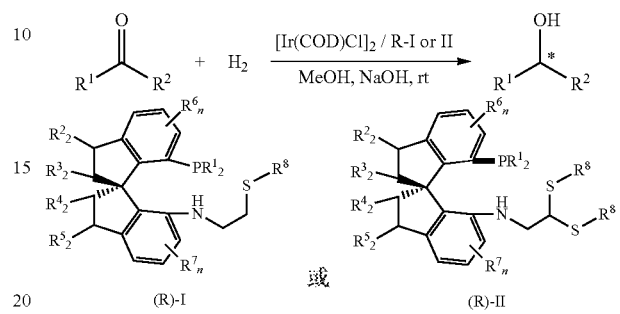

(R)-I or II (1.65 μmol) and [Ir(COD)Cl]$_2$ (0.5 mg, 0.75 μmol) were weighed in a glove box. Then it was sealed standby in a dry, clean 10 mL Schlenk tube with a magnetic stirrer. When taking out, 1 mL of anhydrous methanol was added and stirred at room temperature for 0.5 hour. Under nitrogen atmosphere, the solution was injected with a syringe to a hydrogenation reactor equipped with a glass inner tube and a magnetic stirrer. The gas in the autoclave was replaced three times with hydrogen to adjust the hydrogen pressure to 10 atm (ligand (R)-II, at that time the hydrogen pressure was adjusted to 30 atm). After stirring for 0.5 hour at room temperature, the hydrogen in the autoclave was slowly released. Under a nitrogen atmosphere, was injected to the reactor 7.5~150 mmol substrate (after the solid substrate was dissolved in methanol) and 0.05~25 mmol sodium hydroxide in methanol (0.5 mL (0.1 mmol/mL)~25 mL (1 mmol/mL)). Quickly replace the gas in the reactor with hydrogen three times, and finally adjust the hydrogen pressure to 8~10 atm, the reaction was stirred at room temperature until the hydrogen pressure is no longer reduced. Slowly release the hydrogen in the reactor, use rotary evaporator to remove the solvent from the crude product. After removal of the catalyst by a short silica gel column, the optical purity of the product was analyzed by gas chromatography or nuclear magnetic resonance analysis, and the results of the hydrogenation experiments are shown in Table 1.

TABLE 1

| | Asymmetric catalytic hydrogenation of carbonyl compounds | | | | | |
|---|---|---|---|---|---|---|
| Number | Carbonyl Compound | I or II | S/C | Reaction time (h) | Yield (%) | Ee (%) |
| 1 | Me⟶C(O)CH$_2$C(O)⟶OMe | (R)-Ia | 1000 | 0.5 | 92 | 84 (R) |
| 2 | Me⟶C(O)CH$_2$C(O)⟶OMe | (R)-IIa | 1000 | 0.5 | 92 | 95 (R) |
| 3 | Me⟶C(O)CH$_2$C(O)⟶OMe | (R)-IIa | 100000 | 20 h | 90 | 95 (R) |

TABLE 1-continued
Asymmetric catalytic hydrogenation of carbonyl compounds
| Number | Carbonyl Compound | I or II | S/C | Reaction time (h) | Yield (%) | Ee (%) |
|---|---|---|---|---|---|---|
| 4 | 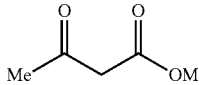 | (R)-IIa | 500000 | 72 | 68 | 93 (R) |
| 5 | 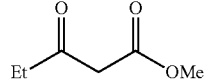 | (R)-IIa | 1000 | 0.5 | 91 | 98 (R) |
| 6 | 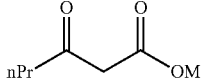 | (R)-IIa | 1000 | 4 | 94 | 98 (R) |
| 7 | 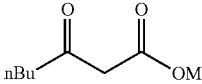 | (R)-IIa | 1000 | 2 | 92 | 98 (R) |
| 8 | 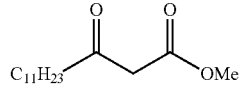 | (R)-IIa | 1000 | 2 | 98 | 98 (R) |
| 9 | 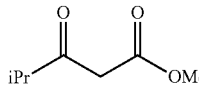 | (R)-IIa | 1000 | 2 | 93 | 98 (S) |
| 10 | 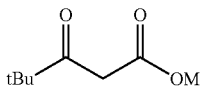 | (R)-IIa | 1000 | 3 | 96 | 99.9 (S) |
| 11 | 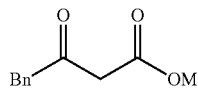 | (R)-IIa | 1000 | 2 | 96 | 98 (R) |
| 12 | 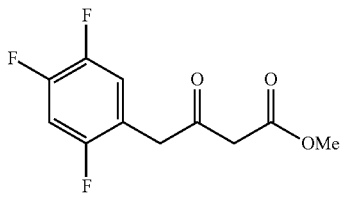 [SMILES: COC(=O)CC(=O)Cc1cc(F)c(F)cc1F] | (R)-IIa | 1000 | 2 | 98 | 99 (R) |
| 13 | 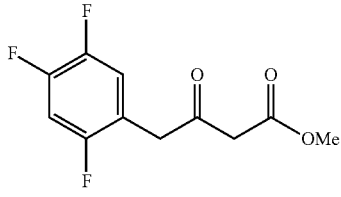 [SMILES: COC(=O)CC(=O)Cc1cc(F)c(F)cc1F] | (R)-IIa | 50000 | 2 | 96 | 99 (R) |
| 14 | 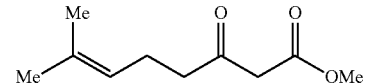 [SMILES: COC(=O)CC(=O)CCC=C(C)C] | (R)-IIa | 1000 | 2 | 95 | 98 (R) |
| 15 | 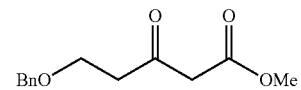 [SMILES: COC(=O)CC(=O)CCOCc1ccccc1] | (R)-IIa | 1000 | 4 | 97 | 98 (S) |
| 16 | 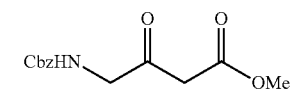 [SMILES: COC(=O)CC(=O)CNC(=O)OCc1ccccc1] | (R)-IIa | 1000 | 0.5 | 92 | 99.9 (S) |

TABLE 1-continued

Asymmetric catalytic hydrogenation of carbonyl compounds

| Number | Carbonyl Compound | I or II | S/C | Reaction time (h) | Yield (%) | Ee (%) |
|---|---|---|---|---|---|---|
| 17 | F$_3$C-CO-CH$_2$-CO-OMe | (R)-IIa | 1000 | 4 | 93 | 95 (S) |
| 18 | Ph-CO-CH$_2$-CO-OMe | (R)-IIa | 1000 | 3 | 96 | 99.9 (S) |
| 19 | Me-CO-CH$_2$-CO-N(Me)$_2$ | (R)-IIa | 1000 | 0.5 | 91 | 90 (S) |
| 20 | Ph-CO-Me | (R)-IIa | 1000 | 8 | 98 | 87 |

The invention claimed is:

1. A chiral spiro phosphine-nitrogen-sulfur tridentate ligand having the structure of Formula I or Formula II, their racemates, optical isomers or their catalytically acceptable salt thereof,

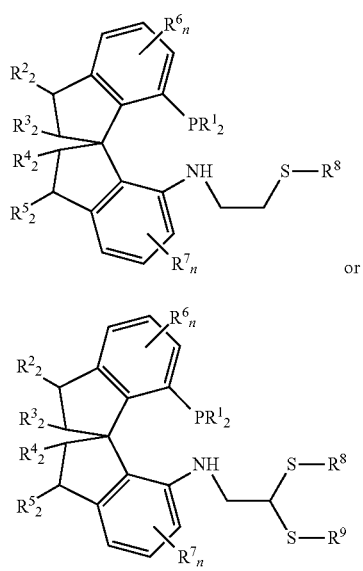

wherein, $R^1$ is selected from $C_1$-$C_{10}$ alkyl, phenyl, substituted phenyl, 1-naphthyl, 2-naphthyl, heteroaryl or benzyl, and the substituent on said phenyl is $C_1$-$C_{10}$ alkyl or alkoxyl, with a substituent amount ranging from 1~5, and said heteroaryl is furyl, thienyl or pyridyl;

$R^2$, $R^3$, $R^4$ and $R^5$ are independently selected from H, $C_1$-$C_{10}$ alkyl, phenyl, substituted phenyl, 1-naphthyl, 2-naphthyl, heteroaryl or benzyl, and the substituent on said phenyl is $C_1$-$C_{10}$ alkyl or alkoxyl, with a substituent amount of 1~5, and said heteroaryl is furyl, thienyl or pyridyl; $C_1$-$C_{10}$ alkoxyl; or $R^2$~$R^3$, $R^4$~$R^5$ are incorporated into $C_3$-$C_7$ aliphatic ring, aromatic ring; $R^2$, $R^3$, $R^4$ and $R^5$ can be the same or different;

$R^6$, $R^7$ are independently selected from H, $C_1$-$C_{10}$ alkyl, $C_1$-$C_{10}$ alkoxy, $C_1$-$C_{10}$ alphatic amido group, and n=0~3; or when n≥2, two adjacent $R^6$ groups or two adjacent $R^7$ groups can be incorporated into a $C_3$-$C_7$ aliphatic ring or aromatic ring and $R^6$, $R^7$ can be same or different;

$R^8$, $R^9$ are independently selected from $C_1$-$C_{10}$ alkyl, $C_1$-$C_{10}$ alkoxy, phenyl, substituted phenyl, 1-naphthyl, 2-naphthyl, heteroaryl or benzyl, and the substituent on said phenyl is $C_1$-$C_{10}$ alkyl or alkoxyl, with a substituent amount of 1~5, and said heteroaryl is furyl, thienyl or pyridyl; or $R^8$ and $R^9$ groups can be incorporated into a ring by $C_2$-$C_4$ carbon chain, carbon chain containing N, O, S, aromatic nucleus or heterocyclic aromatic ring; $R^8$, $R^9$ can be the same or different.

2. A method for synthesizing the chiral spiro phosphine-nitrogen-sulfur tridentate ligand according to claim 1, which is characterized by that, obtained by reacting racemic or optical active compound 7-diary/alkyl phosphine-7'-amino-1,1'-spiro-dihydro-indene shown as Formula 1 having a chiral spiro-dihydro-indene skeleton as the starting material via the following reactions:

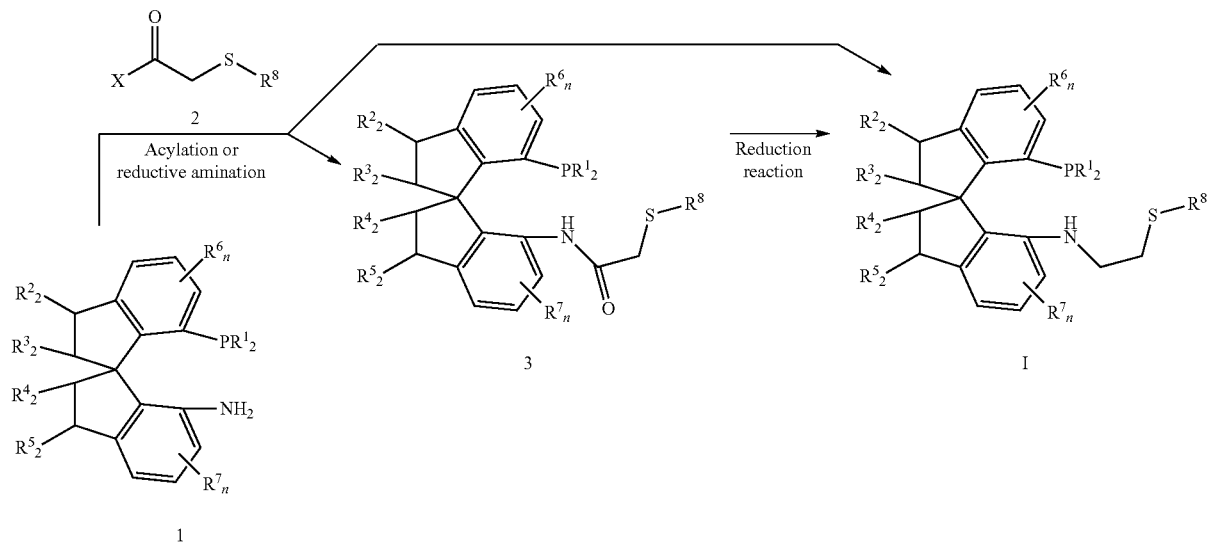

wherein, $R^1 \sim R^9$ of Formula 1, 2, 3 are defined as claim 1, X of Formula 2 is H, Cl, Br, imidazolor hydroxide radical.

3. A method for synthesizing the chiral spiro phosphine-nitrogen-sulfur tridentate ligand according to claim 1, which is characterized by that, obtained by reacting a racemical or optical active compound 7-diary/alkyl phosphine-7'-amino-1,1'-spiro-dihydro-indene shown as Formula 1 having a chiral spiro-dihydro-indene skeleton as the starting material via the following reactions:

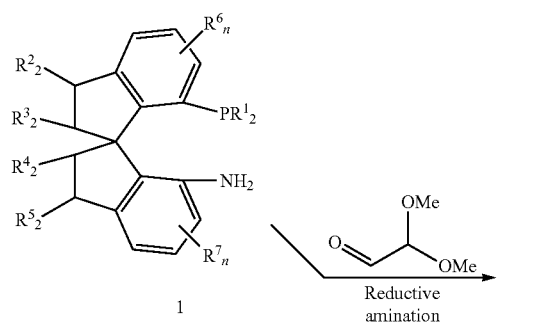

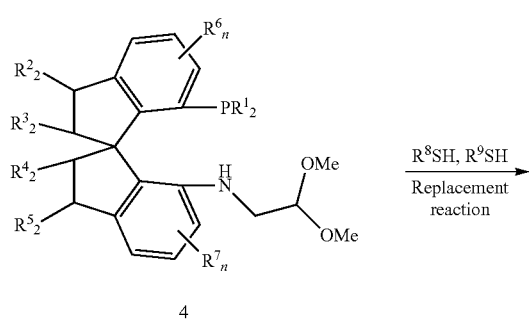

-continued

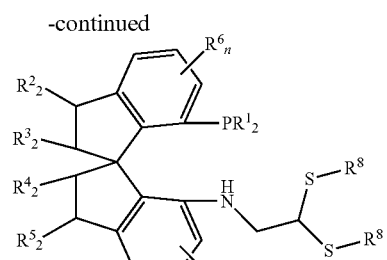

II wherein, $R^1 \sim R^9$ of Formula 1, Formula 4 and Formula II are defined as claim 1.

4. A method for synthesizing the chiral spiro phosphine-nitrogen-sulfur tridentate ligand according to claim 2, wherein, comprising the following steps: the compound of Formula 1 is firstly reacted with the compound of Formula 2 (X is neither H nor OH) in a reactor for 2~24 hours in the presence of an organic solvent and an alkali to obtain the compound shown as Formula 3; the compound of Formula 3 is then reduced to obtain the chiral spiro phosphine-nitrogen-sulfur tridentate ligand having the structure of Formula I; or the compound of Formula 1 is reacted with the compound of Formula 2 (X is H) in a reactor for 2-24 hours in the presence of organic solvent and reducing agent directly to obtain the chiral spiro phosphine-nitrogen-sulfur tridentate ligand having the structure of Formula I.

5. The synthesis method according to claim 4, which is characterized by that, the molar ratio among said compound of Formula 1, Formula 2 and reducing agent is in a range of 1:1~5:1~10; the temperature of the reaction is −20~120° C.

6. A method for synthesizing the chiral spiro phosphine-nitrogen-sulfur tridentate ligand according to claim 2, wherein, comprising the following steps: the compound of Formula 1 is firstly reacted with the compound of Formula 2 (X is OH) in a reactor for 2~24 hours in the presence of an organic solvent, an alkali and hydroxyl activator to obtain the compound shown as Formula 3; the compound of Formula 3 is then reduced to obtain the chiral spiro phosphine-nitrogen-sulfur tridentate ligand having the structure of Formula I.

7. The synthesis method according to claim 6, which is characterized by that, the molar ratio among said compound of Formula 1, Formula 2, hydroxyl activator and reducing agent is in the range of 1:1~5:1~10:1~10; the temperature of the reaction is −20~120° C.

8. A method for synthesizing the chiral spiro phosphine-nitrogen-sulfur tridentate ligand according to claim 2, wherein, comprising the following steps: the compound of Formula 1 is firstly reacted through reduction and amination with the glyoxal-dimethyl-carboxy aldehyde in a reactor in the presence of organic solvent and reducing agent to obtain the compound shown as Formula 4; the compound of Formula 4 is then reacted through replacement reaction with mercaptan ($R^8SH$ and $R^9SH$) in the presence of lewis acid to obtain the chiral spiro phosphine-nitrogen-sulfur tridentate ligand having the structure of Formula II.

9. The synthesis method according to claim 8, which is characterized by that, the molar ratio among said compound of Formula 1, glyoxal-dimethyl-carboxy aldehyde, lewis acid and mercaptan is in the range of 1:1~5:0.1~5:1~10; the temperature of the reaction is −10~120° C.

10. The synthesis method according to claim 4, which is characterized by that, the said organic solvent can be any one of methanol, ethanol, propanol, isopropanol, butanol, tetrahydrofuran, toluene, xylene, methyl tert-butyl ether, diethyl ether, dioxane, N,N-dimethyl-formamide, dimethyl sulfoxide, dichloromethane, chloroform, 1,2-dichloroethane or any mixture thereof; said reducing agent can be lithium aluminium hydride, sodium borohydride, sodium triacetyl borohydride or sodium cyanoborohydride; said alkali is an organic base or an inorganic base, in which said organic base can be pyridine, triethylamine, tributyl amine, N-methyl-morpholine or N,N-diethyl isopropyl amine; said inorganic base can be sodium hydroxide, potassium hydroxide, sodium carbonate or potassium carbonate; said carboxyl-activating reagent is ethyl chloroformate, isopropyl chloroformate, N, N'-dicyclohexyl-carbodiimide or carbonyl diimidazole; said lewis acid can be titanium tetrachloride, boron trifluoride, indium trichloride, zirconium tetrachloride, tellurium tetrachloride, silicotungstic acid, copper sulfate etc.

11. The application of chiral spiro phosphine-nitrogen-sulfur tridentate ligand, their racemates, optical isomers or catalytically acceptable salts thereof according to claim 1, which is characterized by that, comprising reacting the compounds in the asymmetric catalytic hydrogenation reaction to obtain carbonyl compounds, the said carbonyl compounds are selected from β-ketoester compound, β-ketoamide compound or simple ketone compound.

12. The application of chiral spiro phosphine-nitrogen-sulfur tridentate ligand, their racemates, optical isomers or catalytically acceptable salts thereof according to claim 11, which is characterized by that, comprising reacting the said chiral spiro phosphine-nitrogen-sulfur tridentate ligand with the transition metal to obtain a complex, further reacting to obtain carbonyl compounds through the asymmetric catalytic hydrogenation reaction, the said carbonyl compounds are selected from β-ketoester compound, β-ketoamide compound or simple ketone compound.

13. The chiral spiro phosphine-nitrogen-sulfur tridentate ligand, their racemates, optical isomers or catalytically acceptable salts thereof according to claim 1, which is characterized by that, the said compounds is selected from the structures as follows:

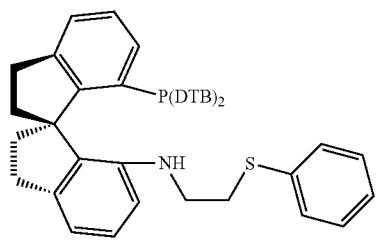

Ia

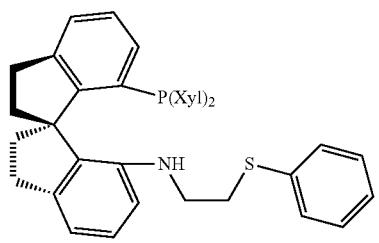

Ib

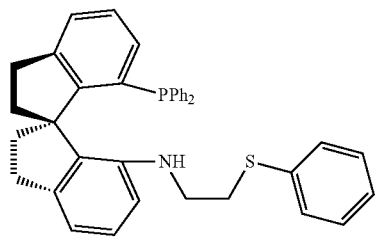

Ic

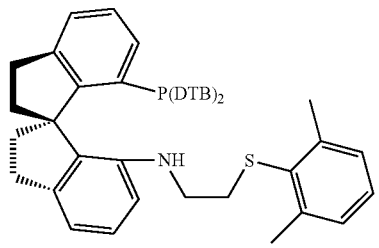

Id

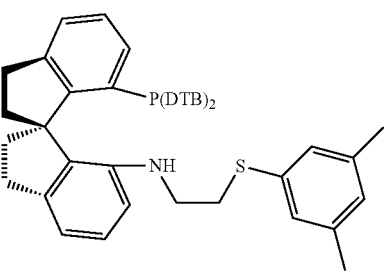

Ie

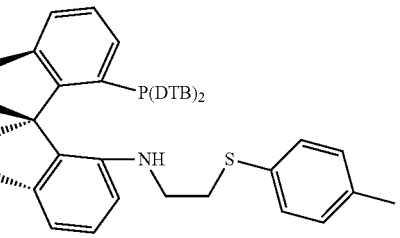

If

Ig
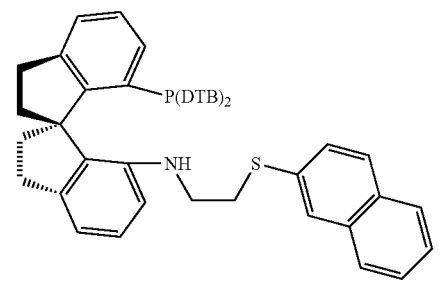
Ih
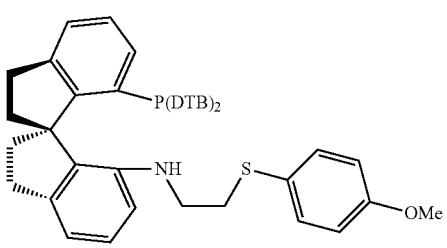
Ii
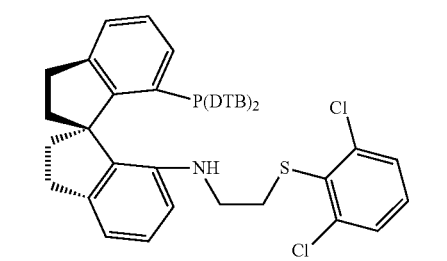
Ij
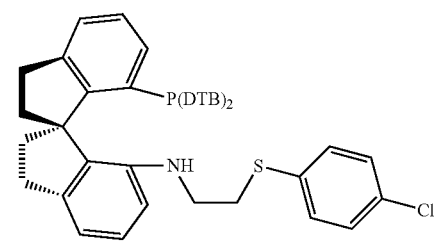
Ik
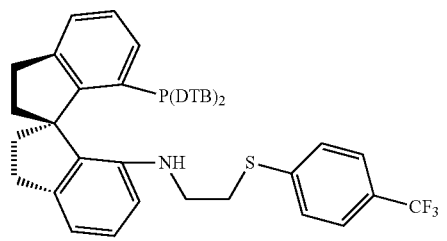
Il
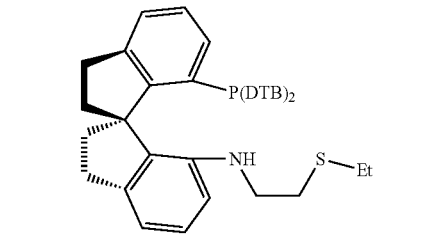
Im
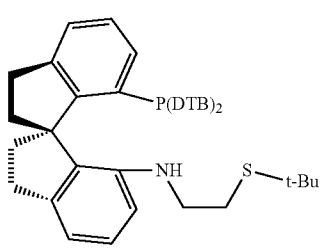
In
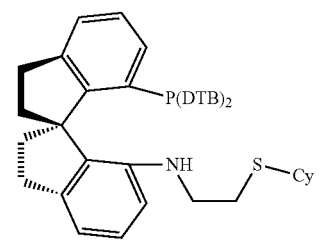
Io
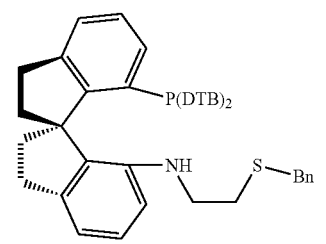
IIa
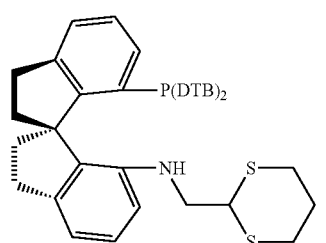
IIb
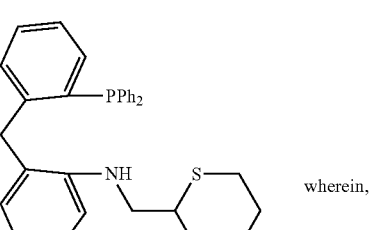
wherein,
DTB is: 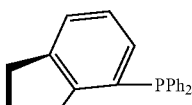
Xyl is: 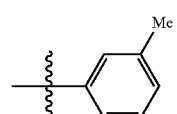
14. The chiral spiro phosphine-nitrogen-sulfur tridentate ligand, their racemates, optical isomers or catalytically acceptable salts thereof according to claim 1, which is characterized by that, the said compounds is selected from the structures as follows:

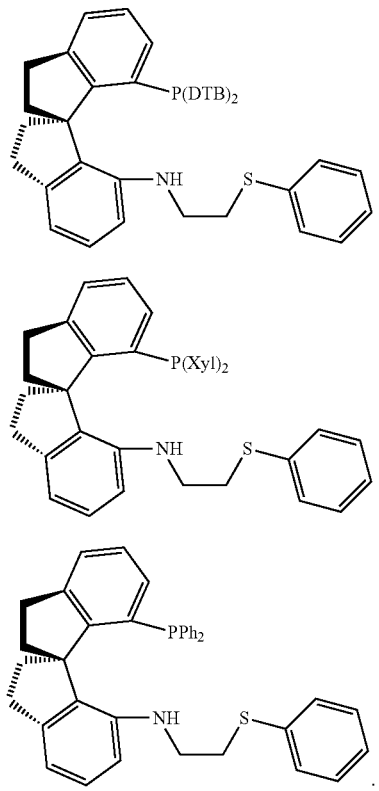

15. The method for synthesizing chiral spiro phosphine-nitrogen-sulfur tridentate ligand their racemates, optical isomers or catalytically acceptable salts thereof according to claim 13, which is characterized by that, comprising the following steps: reacting the chiral spiro phosphine-nitrogen-sulfur tridentate ligand with an transitional metal salt at a temperature of 25~120° C. for 0.5~4 hours in the presence of organic solvent; and then stirred for 0.1~3 hours under the hydrogen atmosphere at the pressure of 0.1~50 atm to obtain the required chiral catalysts; the molar ratio among the said chiral spiro phosphine-nitrogen-sulfur tridentate ligand and an transitional metallic salt is in the range of 1:1~2:1; the said iridium metal salt is [Ir(COD)Cl]$_2$ (COD=Cyclooctadiene), [Ir(COD)$_2$]BF$_4$, [Ir(COD)$_2$]PF$_6$, [Ir(COD)$_2$]SbF$_6$ or [Ir(COD)$_2$]OTf.

16. The method for synthesizing chiral spiro phosphine-nitrogen-sulfur tridentate ligand, their racemates, optical isomers or catalytically acceptable salts thereof according to claim 13, which is characterized by that, further comprising reacting the said chiral compounds directly to obtain carbonyl compounds through the asymmetric catalytic hydrogenation reaction with or without the treatment of dissolving process to form a storable solid, the said carbonyl compounds are selected from β-ketoester compound, β-ketoamide compound or simple ketone compound.

17. A method for synthesizing a chiral alcohol compound, which is characterized by that, comprising reacting the ligand complex synthesized in claim 13 as a chiral catalyst with carbonyl compounds and alkalis under the hydrogen atmosphere at the pressure of 0.1~100 atm and at the temperature of at 0~80° C. to obtain the chiral alcohol compound.

18. The method for synthesizing the chiral alcohol compound according to claim 17, which is characterized by that, the molar ratio among the said carbonyl compound and the said ligand is in the range of 100:1~500000:1 (the used amount of catalyst is 1~0.0002 mol %); The concentration of the substrate is 0.001~10.0 M; The said alkali is selected from sodium hydroxide, potassium hydroxide, sodium carbonate, potassium carbonate, sodium ethoxide, potassium ethoxide, sodium tert-butoxide, potassium tert-butoxide, lithium tert-butoxide, triethyl amine, tributyl amine or N-methyl morpholine; the concentration of the said alkali is 0.005 M~1.0M; the temperature of the reaction is 0~80° C.

19. The synthesis method according to claim 15 or 17, which is characterized by that, the said organic solvent is any one of methanol, ethanol, propanol, isopropanol, butanol, tetrahydrofuran, toluene, methyl tert-butyl ether, dioxane, DMF, DMSO or any mixture thereof.

* * * * *